(12) United States Patent
Wise

(10) Patent No.: US 9,700,549 B2
(45) Date of Patent: Jul. 11, 2017

(54) COMPOSITIONS AND METHODS FOR TREATING PELVIC PAIN AND OTHER CONDITIONS

(71) Applicant: David Wise, San Francisco, CA (US)

(72) Inventor: David Wise, San Francisco, CA (US)

(*) Notice: Subject to any disclaimer, the term of this patent is extended or adjusted under 35 U.S.C. 154(b) by 0 days.

(21) Appl. No.: 14/506,551

(22) Filed: Oct. 3, 2014

(65) Prior Publication Data

US 2015/0150863 A1    Jun. 4, 2015

Related U.S. Application Data

(60) Provisional application No. 61/886,244, filed on Oct. 3, 2013, provisional application No. 61/898,095, filed on Oct. 31, 2013, provisional application No. 61/924,635, filed on Jan. 7, 2014, provisional application No. 61/936,031, filed on Feb. 5, 2014, provisional application No. 61/982,614, filed on Apr. 22, 2014, provisional application No. 62/014,945, filed on Jun. 20, 2014, provisional application No. 62/051,249, filed on Sep. 16, 2014.

(51) Int. Cl.

| A61K 31/44 | (2006.01) |
|---|---|
| A61K 31/4422 | (2006.01) |
| A61K 31/554 | (2006.01) |
| A61K 45/06 | (2006.01) |
| A61K 31/167 | (2006.01) |
| A61K 31/198 | (2006.01) |
| A61K 31/573 | (2006.01) |
| A61K 9/00 | (2006.01) |
| A61M 29/00 | (2006.01) |
| A61K 9/02 | (2006.01) |
| A61K 47/10 | (2017.01) |
| A61K 47/14 | (2017.01) |
| A61K 9/06 | (2006.01) |
| A61K 47/44 | (2017.01) |

(52) U.S. Cl.
CPC ........ *A61K 31/4422* (2013.01); *A61K 9/0031* (2013.01); *A61K 9/02* (2013.01); *A61K 31/167* (2013.01); *A61K 31/198* (2013.01); *A61K 31/554* (2013.01); *A61K 31/573* (2013.01); *A61K 45/06* (2013.01); *A61M 29/00* (2013.01); *A61K 9/06* (2013.01); *A61K 47/10* (2013.01); *A61K 47/14* (2013.01); *A61K 47/44* (2013.01)

(58) Field of Classification Search
None
See application file for complete search history.

(56) References Cited

U.S. PATENT DOCUMENTS

| 3,536,809 A | 10/1970 | Applezweig |
|---|---|---|
| 3,598,123 A | 8/1971 | Zaffaroni |
| 3,845,770 A | 11/1974 | Theeuwes et al. |
| 3,916,899 A | 11/1975 | Theeuwes et al. |

(Continued)

FOREIGN PATENT DOCUMENTS

| EP | 2322177 | 7/2014 |
|---|---|---|
| WO | WO 9506466 | 3/1995 |

(Continued)

OTHER PUBLICATIONS

Santis et al (Drug Dev Ind Pharm 37:1098-1106, 2013—published online Aug. 20, 2012).*
Weiss et al (Contemporary OB/GYN 57(10):38-46 Oct. 2012).*
Pastore et al (J Obstet Gynecol Neonatal Nurs 41:680-691, 2012 (published online Aug. 3, 2012)).*
Hou et al (Am J Phys Med Rehabil 81:342-349, 2002 (Abstract only)).*
Lee et al (J Exercise Rehabilitation 11:108-111, 2015).*
Cohen et al (Anesthesiology 101:495-526, 2004).*
Agrawal, et al., "Randomized Controlled Pilot Trial of Nefidipine as Oral Therapy vs. Topical Application in the Treatment of Fissure-in-ano" American Journal of Surgery, vol. 206 Issue 5, Nov. 2013 pp. 748-751 Abstract only.

(Continued)

*Primary Examiner* — Craig Ricci
(74) *Attorney, Agent, or Firm* — Hoxie & Associates LLC

(57) ABSTRACT

Methods are provided for treating conditions including chronic pelvic pain, in which there are palpable trigger points of local areas of muscle restriction and spasticity that recreate or refer pain of patients complaints upon palpation, chronic pelvic pain syndrome, pelvic floor myalgia, pelvic floor dysfunction, interstitial cystitis, levator ani syndrome, coccygodynia, prostatodynia, piriformis syndrome, anal sphincter pain, bowel movement pain, post bowel movement pain, ejaculatory pain, post ejaculatory pain, sitting pain, post bowel movement pain, rectal pain, tailbone pain, urinary frequency, urinary urgency, urinary hesitancy, post urinary pain, overactive bladder, perineal pain, penile pain, vaginismus, anismus, sexual dysfunction, reduced level of ejaculate or reduced penile erection, myofascial pain in muscle tissue of a patient who has one or more trigger points in the muscle tissue, or the pain/sensitivity of pelvic floor muscle trigger points and specific areas of myofascial restriction detected upon palpation in a patient comprising administering to the one or more trigger points of the patient in need thereof a therapeutically effective amount of a calcium channel blocker, or L-arginine, or a combination of a calcium channel blocker and L-arginine, or pharmaceutically acceptable salts, hydrates, solvates and prodrugs thereof; the application of the topical form of the drug can be applied by the patient regularly as part of a self treatment program to heal muscle related pain and muscle related pelvic pain and each optionally together with a corticosteroid such as cortisone of hydrocortisone. The invention further provides methods for myofascial release, trigger point release, and the use of dilators with and without calcium channel blockers for pain conditions. The invention further provides pharmaceutical compositions, kits and applicator devices useful in the methods of the invention.

17 Claims, 6 Drawing Sheets

(56) References Cited

U.S. PATENT DOCUMENTS

| | | | |
|---|---|---|---|
| 4,008,719 A | 2/1977 | Theeuwes et al. |
| 4,328,245 A | 5/1982 | Yu |
| 4,409,239 A | 10/1983 | Yu |
| 4,410,545 A | 10/1983 | Yu |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,698,220 A | 12/1997 | Cardinal et al. |
| 5,733,566 A | 3/1998 | Lewis |
| 5,739,108 A | 4/1998 | Mitchell |
| 5,798,119 A | 8/1998 | Herbig et al. |
| 5,871,775 A | 2/1999 | Valducci |
| 5,891,474 A | 4/1999 | Busetti et al. |
| 5,922,356 A | 7/1999 | Koseki et al. |
| 5,972,891 A | 10/1999 | Kamei et al. |
| 5,980,945 A | 11/1999 | Ruiz |
| 5,993,855 A | 11/1999 | Yoshimoto et al. |
| 6,045,830 A | 4/2000 | Igari et al. |
| 6,087,324 A | 7/2000 | Igari et al. |
| 6,113,943 A | 9/2000 | Okada et al. |
| 6,197,350 B1 | 3/2001 | Yamagata et al. |
| 6,248,363 B1 | 6/2001 | Patel et al. |
| 6,264,970 B1 | 7/2001 | Hata et al. |
| 6,267,981 B1 | 7/2001 | Okamoto et al. |
| 6,350,458 B1 | 2/2002 | Modi |
| 6,376,461 B1 | 4/2002 | Igari et al. |
| 6,391,869 B1 | 5/2002 | Parks et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada |
| 7,198,800 B1 | 4/2007 | Ko |
| 8,048,875 B1 | 11/2011 | Kamm et al. |
| 8,224,464 B2 | 7/2012 | Wise |
| 8,318,721 B2 | 11/2012 | Kamm et al. |
| 8,337,435 B2 | 12/2012 | Wise |
| 8,632,482 B2 | 1/2014 | Wise |
| 8,639,360 B2 | 1/2014 | Wise |
| 2002/0032188 A1 | 3/2002 | Jossifoff |
| 2002/0155539 A1 | 10/2002 | Ruben et al. |
| 2003/0114394 A1 | 6/2003 | Levine et al. |
| 2004/0028752 A1 | 2/2004 | Kamm et al. |
| 2004/0198775 A1 | 10/2004 | Fraser et al. |
| 2005/0101936 A1 | 5/2005 | Gonzales et al. |
| 2008/0182841 A1* | 7/2008 | Levine ................ A61K 9/0034 514/211.07 |
| 2008/0292560 A1 | 11/2008 | Tamarkin et al. |
| 2010/0197693 A1 | 8/2010 | Zhang et al. |
| 2010/0239635 A1 | 9/2010 | McClain et al. |
| 2011/0244043 A1 | 10/2011 | Xu et al. |
| 2011/0263568 A1 | 10/2011 | Kamm et al. |
| 2012/0165285 A1 | 6/2012 | Richardson |
| 2013/0079332 A1 | 3/2013 | Kamm et al. |
| 2013/0189354 A1 | 7/2013 | Singh |
| 2013/0345240 A1 | 12/2013 | Whitten et al. |

FOREIGN PATENT DOCUMENTS

| | | |
|---|---|---|
| WO | WO 97/18782 | 5/1997 |
| WO | WO 9836733 | 8/1998 |
| WO | WO 9837886 | 9/1998 |
| WO | WO 0217918 | 3/2002 |
| WO | WO 03037381 | 5/2003 |
| WO | WO 2008022032 | 2/2008 |
| WO | WO 2009033489 | 3/2009 |
| WO | WO 2011006073 | 1/2011 |
| WO | WO 2011/042420 | 4/2011 |
| WO | WO 2011072012 | 6/2011 |
| WO | WO 2013110077 | 7/2013 |
| WO | WO 2013171726 | 11/2013 |
| WO | WO 2015/051336 | 4/2015 |

OTHER PUBLICATIONS

Anal Fissures "Diseases of the Rectum and Anus" Jan 24, 2008 Abstract only.

Agaoglu, et al., "Oral Nifedipine in the Treatment of Chronic Anal Fissure" Digestive Surgery 2003; vol. 20 (5) pp. 452-456 Abstract only.

Biller, A Study Examining the Use of Vaginal Nifedipine With Pelvic Floor Physical Therapy for Levator Myalgia and Pelvice Pain, Apr. 20, 2012 Vanderbilt University, Clinical Trials.gov NCT01586286.

Brisinda, et al., "Oral Nifedipine Reduces Resting Anal Pressure and Heals Chronic Anal Fissure" British Journal of Surgery, vol. 87, Issue 2, p. 251 Feb. 2000 Abstract not available.

Brune, et al. "(−)-(9S)-9-(3-Bromo-4-fluorophenyl)-2,3,5,6,7,9-hexahyothieno[3,2-b]quinolin-8(4H)-one 1,1-dioxide (A-278637): A Novel ATP-Sensitive Potassium Channel Opener Efficacious in Suppressing Urinary Bladder Contractions. II. In Vivo Characterization", J Pharmacol Exp Ther, Oct. 1, 2002, vol. 303, pp. 387-394.

Carapeti, et al., "Topical Diltiazem and Bethanechol Decrease Anal Sphincter Pressure an Heal Anal Fissures Without Side Effects" Dis Colon Rectum, Oct. 2000; 43; pp. 1359-1362.

Chrysos, et al., "Effect of Nifedipine on Rectoanal Motility" Dis Colon Rectum Feb. 1996; vol. 3(2) pp. 212-216 Abstract only.

Cook, et al., Oral Nifedipine Reducs Resting Anal Pressure and Heals Chronic Anal Fissure, British Journal of Surgery 1999, vol. 86 pp. 1269-1273 Abstract only.

De Rosa, et al., Conservative Versus Surgical Treatment for Chronic Anal Idiopathic Fissure: a Prospective Randomized Trial, Sep. 2013, vol. 65, Issue 3, pp. 197-200.

Gentile, et al., "LigaSure Haemorrhoidectomy versus Conventional Diathermy for IV-Degree Haemorrhoids: Is it the Treatment of Choice? A Randomized, Clinical Trial" International Scholarly Research Network ISRN Gastroenterology, vol. 2011, Article ID 467258, Sep. 8, 2010, pp. 1-7.

Golfam, F. et al.,"The Effect of Topical Nifedipine in Treatment of Chronic Anal Fissure", Acta Medica Iranica, vol. 48 No. 5 (2010) pp. 295-299.

Ho, et al., "Randomized Clinical Trial Comparing Oral Nifedipine with Lateral Anal Sphincterotomy and Tailored Sphincterotomy in the Treatment of Chronic Anal Fissure" British Journal of Surgery 2005 Apr;92(4) pp. 403-408 Abstract only.

Kimmell, et al., "Anorectal Fissures: An Under-Recognized Cause of Low Back Pain? Case Report" Journal Oklahoma State Med Assoc. Jan. 2010; vol. 103 (1):10-2 Abstract only.

Knight, et al. "Topical Diltiazem Ointment in the Treatment of Chronic Anal Fissure" British Journal of Surgery 2001, 88, pp. 553-556.

McCallion, et al., "Progress in the Understanding and Treatment of Chronic Anal Fissure" Postgraduate Medical Journal, 2001 vol. 77 pp. 753-758.

Mustafa, et al. "Comparison of Topical Glyceryl Trinitrate Ointment and Oral Nifedipine in the Treatment of Chronic Anal Fissure" Acta Chir Belg. Jan.-Feb. 2006; 106(1):55-8 Abstract only.

Thwayeb "Randomised Clinical Trial of Effect of Oral Nifedipine on Pain and Healing After Hemorrhoidectomy" Eastern Journal of Medicine 12 (2007) pp. 15-20.

Tranqui, et al., "Nonsurgical Treatment of Chronic Anal Fissure: Nitroglycerin and Dilation Versus Nifedipine and Botulinum Toxin" Canadian Journal of Surgery Feb. 2006;49(1) pp. 41-45 Abstract only.

Turkish Journal of Surgery, 2001, vol. 17, Issue 6 pp. 343-350 Abstract only.

Zhang, et al., "Impact of BKCa Channel in Prostate Smooth Muscle Cells on the Membrane Potential in Rats with Chronic Abacterial Prostatitis" Jan. 2013, vol. 19 (1) Abstract only.

(56) References Cited

OTHER PUBLICATIONS

PCT/US2014/059188 International Search Report and Written Opinion dated Jan. 21, 2015.
Anderson et al., "Painful Myofascial Trigger Points and Pain Sites in Men With Chronic Prostatitis/Chronic Pelvic Pain Syndrome", J Urol., 182 (6): 2753-8, Oct. 2009. (Abstract Only).
Anderson et al., "6-Day Intensive Treatment Protocol for Refractory Chronic Prostatitis/Chronic Pelvic Pain Syndrome Using Myofascial Release and Paradoxical Relaxation Training", Journal of Urology, 185(4):1294-1299, Apr. 2011.
Anderson et al., "Drug Therapies for CP/CPPS: Help or Hype?", Nature Reviews Urology, 8: 236-237, May 2011.
Anderson et al., "Integration of Myofascial Trigger Point Release and Paradoxical Relaxation Training Treatment of Chronic Pelvic Pain in Men", Journal of Urology, 174(1):155-60, Jul. 2005.
Anderson et al., "Psychometric Profiles and Hypothalamic-Pituitary-Adrenal Axis Function in Men with Chronic Prostatitis/Chronic Pelvic Pain Syndrome", Journal of Urology, 179:956-960, Mar. 2008.
Anderson et al., Safety and Effectiveness of an Internal Pelvic Myofascial Trigger Point Wand for Urological Chronic Pelvic Pain Syndrome (UCPPS), American Urological Association, Apr. 2011, Abstract Presentation.
Anderson et al., Safety and Effectiveness of an Internal Pelvic Myofascial Trigger Point Wand for Urological Chronic Pelvic Pain Syndrome, Clin. J. Pain., 27(9):764-8, Nov. 2011. (Abstract Only).
Anderson et al., "Sexual Dysfunction in Men with Chronic Prostatitis/Chronic Pelvic Pain Syndrome: Improvement After Trigger Point Release and Paradoxical Relaxation Training", The Journal of Urology, 176(4 Pt 1):1534-1538, Oct. 2006.
Anita L. Nelson, "Chronic Pelvis Pain and Dysmenorrhea", presentation, Harbor-UCLA Medical Center, pp. 1-15, Apr. 10, 2008.
"American Urological Association Meetings Honor Internal Trigger Point Wand Study of the Wise-Anderson Protocol", American Urological Association, 2011, 2 pages.
Bornstein et al., "Topical Nifedipine For The Treatment of Localized Provoked Vulvodynia: A Placebo-Controlled Study" J. Pain 11(12): 1403-1409, Dec. 2010. (Abstract Only).
Brisinda et al., "Oral Nifedipine Reduces Resting Anal Pressure and Heals Chronic Anal Fissure", British Journal of Surgery, 87(2):251, Feb. 2000, Published Online: Dec. 10, 2002.
Ezri et al., "Topical Nifedipine vs. Topical Glyceryl Trinitrate for Treatment of Chronic Anal Fissure", Diseases of the Colon & Rectum, 46(6):805-808, Jun. 2003. (Abstract Only).
Gosselink et al., "Treatment of chronic anal fissure by application of L-arginine gel: a phase II study in 15 patients.", Dis Colon Rectum., 48(4): 832-837, Apr. 2005. (Abstract Only).
Langer, "New methods of drug delivery", Science, 249(4976):1527-1533, Sep. 1990. (Abstract Only).
"New Article Reports Wise-Anderson Protocol Helps 82% of Men Diagnosed With Prostatitis", Journal of Urology 2010 study, TheDoctor'sChannel.com, 3 pages, (http://www.pelvicpainhelp.com/wp-content/uploads/2014/10/1_Doctors_Channel_complete.pdf) Date Accessed: May 4, 2016.
"Self-massage shows benefit in CP/CPPS patients with myofascial pain", Urology Times, May 19, 2011, 2 pages, (http://urologytimes.modernmedicine.com/urologytimes/Modern+Medicine+News/AUA-2011-Self-massage-shows-benefit-in-CPCPPS-pati/ArticleStandard/Article/detail/723402) Date Accessed: May 5, 2016.
Shaikh, et al., Mucoadhesive Drug Delivery Systems, J. Pharm. Bioallied Sci. 3(1):89-100, Jan.-Mar. 2011.
Stein, "Intensive Therapy Regimen Helps Men with Chronic Pelvic Pain Syndrome", Medscape Medical News, Jun. 1, 2010, 3 pages.
Stein, "Trigger Point Wand Eases Chronic Pelvic Pain" Medscape Medical News, May 23, 2011, 3 pages.
Wise et al., A Headache in the Pelvis: A New Understanding and Treatment For Chronic Pelvic Pain Syndromes, 6th ed.; National Center for Pelvic Pain Research; pp. 1-565, 2014.
Yuan et al., "Thermosensitive and mucoadhesive in situ gel based on poloxamer as new carrier for rectal administration of nimesulide." Int. J. Pharm., vol. 430 (1-2): 114-9, Apr. 2012. (Abstract Only).

\* cited by examiner

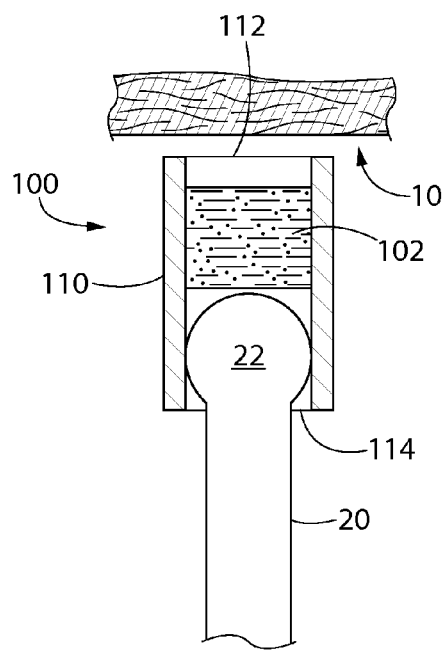
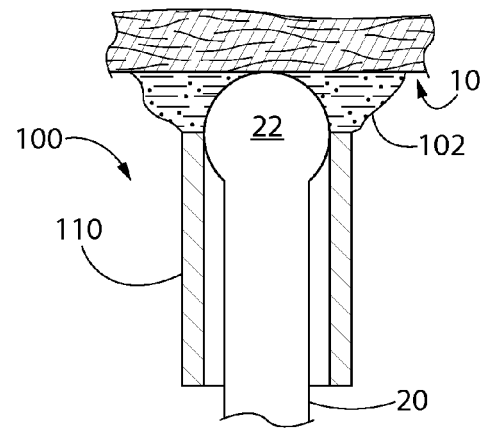
FIG. 1A
FIG. 1B
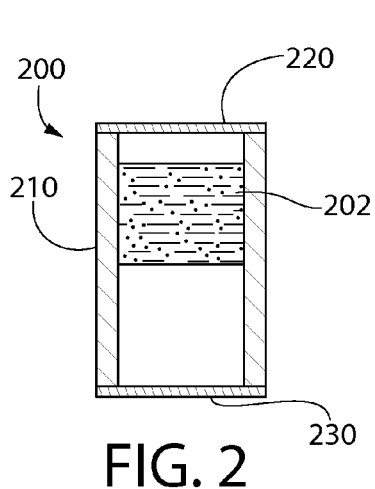
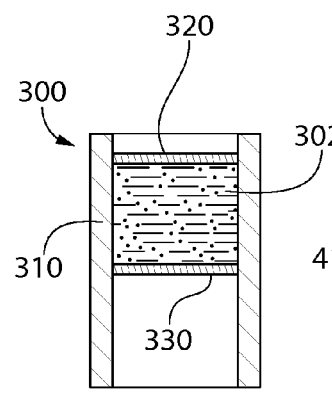
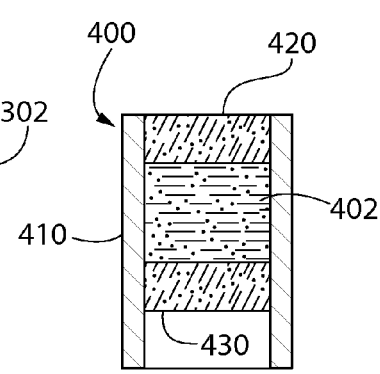
FIG. 2
FIG. 3
FIG. 4

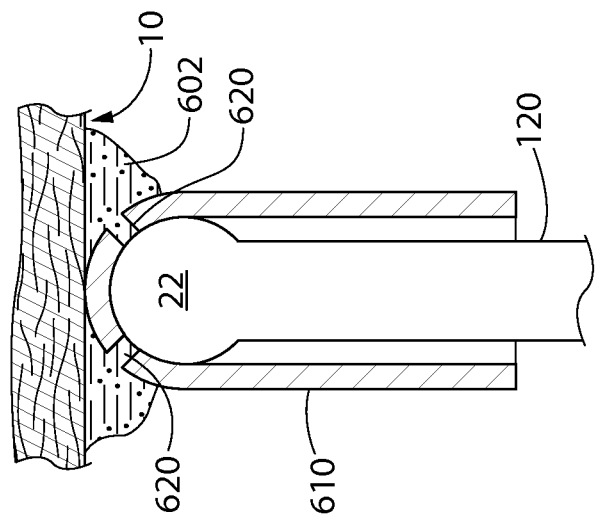
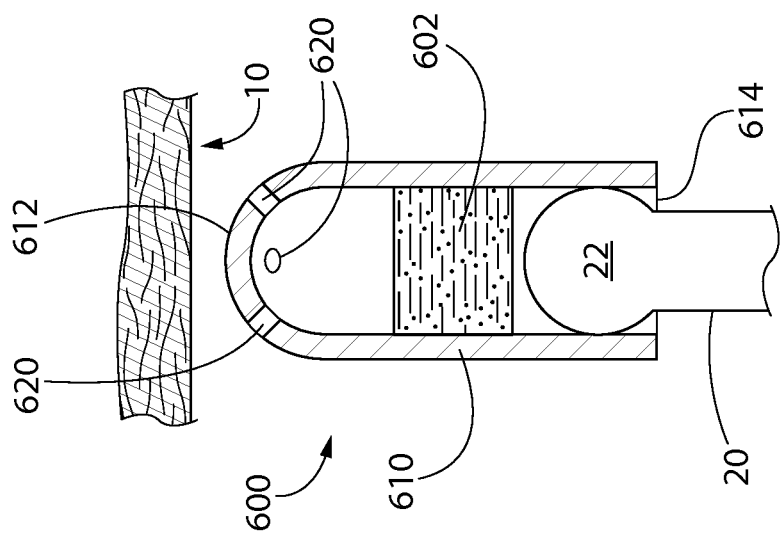

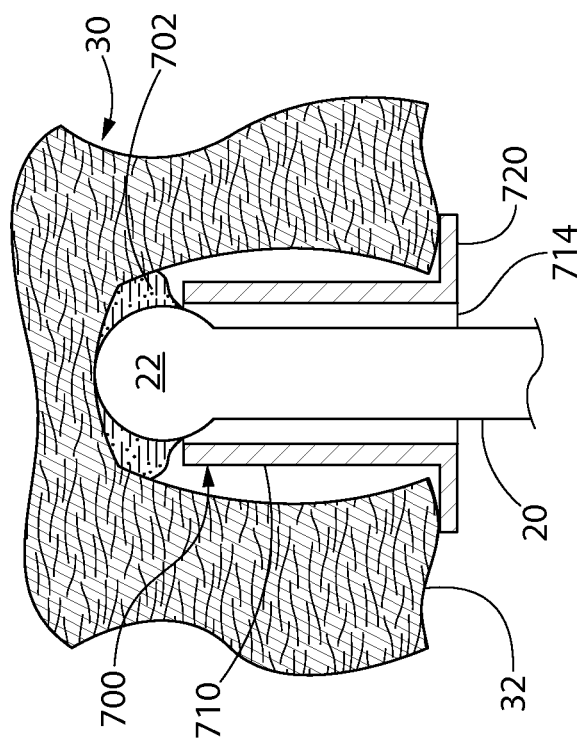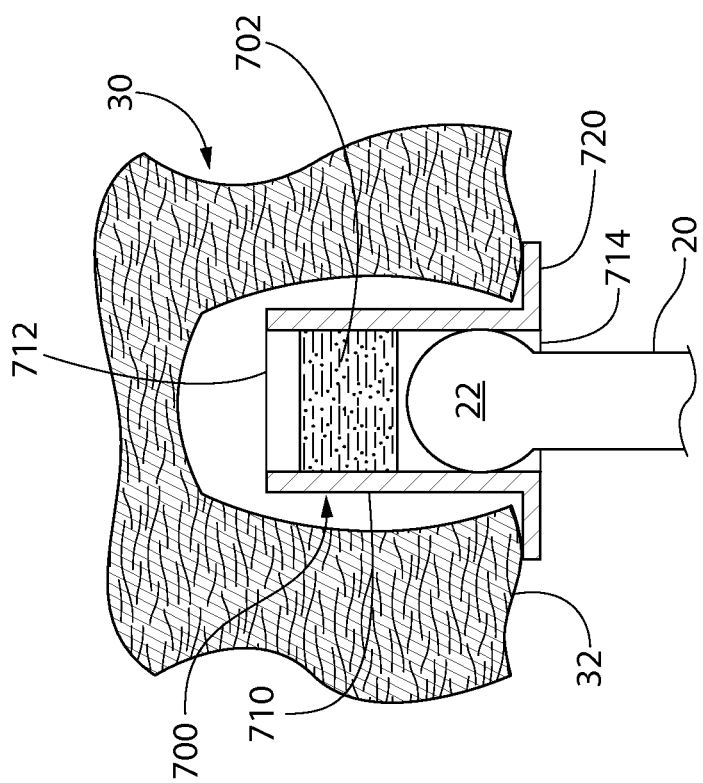

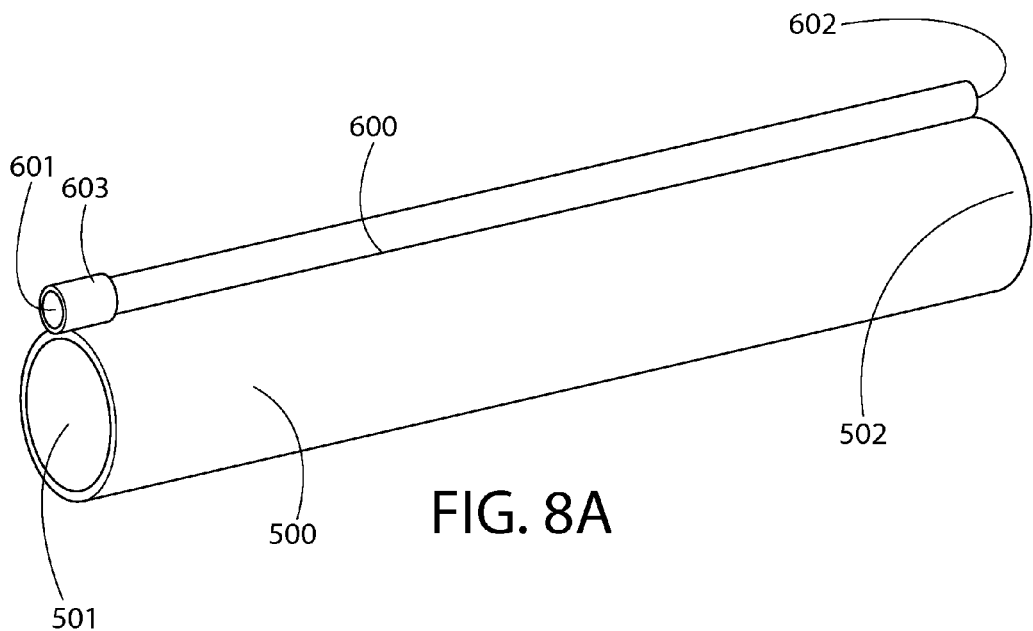
FIG. 8A
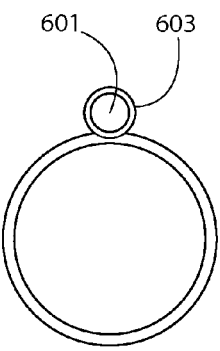   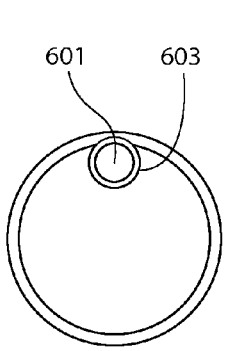   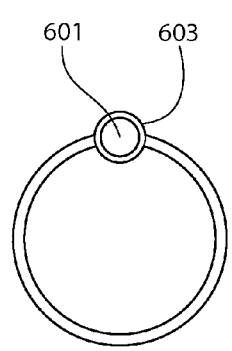
FIG. 8B            FIG. 8C            FIG. 8D

COMPOSITIONS AND METHODS FOR TREATING PELVIC PAIN AND OTHER CONDITIONS

CROSS REFERENCE TO RELATED APPLICATIONS

This application claims priority benefit of U.S. Provisional Application Ser. Nos. 61/886,244 filed Oct. 3, 2013; 61/898,095 filed Oct. 31, 2013; 61/924,635 filed Jan. 7, 2014; 61/936,031 filed Feb. 5, 2014; 61/982,614 filed Apr. 22, 2014; 62/014,945 filed Jun. 20, 2014 and 62/051,249, filed Sep. 16, 2014. The entire disclosures of each of the foregoing applications is incorporated herein by reference in their entireties.

BACKGROUND

The disclosure herein relates to drugs, drug delivery devices, and methods for treating pain conditions, and in particular pelvic pain, in women and men Pelvic pain has long been a problem among women and men. Conventional medicine has treated pelvic pain in various ways including, 1) an organ-specific focus in which pelvic pain is believed to be a symptom of inflammation in the bladder, inflammation or infection in the prostate gland, or pathology of the uterus; 2) focus on the idea of the pudendal nerve being entrapped and needing release; 3) focus on an autoimmune process; or 4) focus supposed on psychiatric problems, a propensity toward malingering, or neurotic somatization.

The approaches described above are based on a misunderstanding of the nature of most cases of pelvic pain. In recent years, evidence has emerged that a large majority of pelvic pain in men and women is related to the presence of trigger points and myofascial dysfunction and trigger point related myofascial pain. Understanding cases of pelvic pain as muscle related pain is an entirely new paradigm in urology. This new understanding sees anxiety and sometimes injury producing trigger points within muscles either at the surface of the muscle, inside the muscle, in the belly or the attachment of the muscle of the pelvic floor. These trigger points are painful bands in muscle that can refer pain to remote sites, and when pressed skillfully recreate a patient's symptoms. When pressed in a specific way these trigger points can release, often attended by a significant reduction or abatement in pain and dysfunction. Pelvic floor trigger points and related myofascial restriction have typically been found to be strongly exacerbated by muscle overuse, local ischemia, psychological anxiety and other perpetuating factors. Trigger point release, particularly for trigger points located on the outside of the body has become a subspecialty within medicine. The inventor of the present invention, David Wise, Ph.D., along with his colleague and co-author Rodney Anderson, M.D., professor of urology at Stanford University, previously described techniques for identifying and releasing trigger points in their book *A Headache in the Pelvis: A New Understanding and Treatment for Prostatitis and Chronic Pelvic Pain Syndromes*, which was originally published by the National Center for Pelvic Pain Research in 2003, and is incorporated herein by reference in its entirety. He is an author of four other peer-reviewed articles on this subject.

Topical nifedipine has been reported for use in anal fissure and vulvodynia. See e.g., Bornstein, J. et al., J. Pain 2010 11(12): 1403-1409. A clinical trial also is ongoing for the use of vaginal nifedipine as an adjunct to conventionally delivered pelvic floor physical therapy for levator myalgia and pelvic pain. See Clinical Trial No. NCT01586286 (Vanderbilt Univ.) at clinicaltrials.gov. However, these studies neither describe nor suggest the specific application of calcium channel blockers or L-arginine to specific muscle trigger points; or the use of the compounds as disclosed herein.

In an age where there is an epidemic of the use of narcotic medication to treat pelvic pain, there exists an ongoing need for more efficacious treatments for the pain conditions described above. This invention is directed to these, as well as other, important ends.

SUMMARY

Drugs, drug delivery devices, and methods for treating pelvic pain are taught herein.

In one aspect, methods are provided for treating, reducing, resolving, eliminating, and/or preventing prostatitis category IIIA and/or IIIB in a male patient. In some embodiments, the method comprises administering to the male patient in need thereof a therapeutically effective amount of a calcium channel blocker (also known as a calcium channel antagonist), or L-arginine, or a combination of a calcium channel blocker and L-arginine, or pharmaceutically acceptable salts, hydrates, solvates and prodrugs thereof.

In a further aspect, methods are provided for treating, reducing, resolving, eliminating, and/or preventing chronic pelvic pain, chronic pelvic pain syndrome, pelvic floor myalgia, pelvic floor dysfunction, interstitial cystitis, levator ani syndrome, coccygodynia, prostatodynia, prostadynia, piriformis syndrome, anal sphincter pain, bowel movement pain, post bowel movement pain, overactive bladder, ejaculatory pain, ejaculatory discomfort, post ejaculatory pain, sitting pain, rectal pain, tailbone pain, urinary frequency, urinary urgency, urinary hesitancy, perineal pain, penile pain, vaginismus, anismus, sexual dysfunction, anal fissures, reduced level of ejaculate or reduced penile erection, nonbacterial prostatitis, slow urinary flow, reduced urinary flow, post ejaculatory discomfort, myofascial pain in muscle tissue of a patient who has one or more trigger points in the muscle tissue, or the pain/sensitivity of pelvic floor muscle trigger points and specific areas of myofascial restriction detected upon palpation in a patient.

In a further aspect, methods are provided for reducing or resolving trigger point activity in a muscle of a patient comprising contacting the muscle with a therapeutically effective amount of a calcium channel blocker, or L-arginine, or a combination of a calcium channel blocker and L-arginine, or pharmaceutically acceptable salts, hydrates, solvates and prodrugs thereof.

In a further aspect, the methods of the invention as described herein include administering to the patient in need thereof a therapeutically effective amount of a calcium channel blocker, or L-arginine, or a combination of a calcium channel blocker and L-arginine, or pharmaceutically acceptable salts, hydrates, solvates and prodrugs thereof, optionally together with a corticosteroid, for example cortisone or cortisol.

In a further aspect, the methods of the invention described herein include treating a patient in need thereof with a dilator, such as an anal, vaginal or urethral dilator (including pediatric dilators thereof). In a further embodiment, treatment with such dilators may further comprise the oral or topical administration of one or more calcium channel blockers, or pharmaceutically acceptable salts, hydrates, solvates or prodrugs thereof.

In some further embodiments, methods are provided for treating urinary sphincter spasm and post urinary pain; and for treating proctalgia fugax, comprising administering to a patient in need thereof a therapeutically effective amount of a calcium channel blocker, for example nifedipine or diltiazem, or pharmaceutically acceptable salts, hydrates, solvates and prodrugs thereof. In some embodiments, the calcium channel blocker or pharmaceutically acceptable salts, hydrates, solvates and prodrugs thereof is administered orally, and in some embodiments, the calcium channel blocker or pharmaceutically acceptable salts, hydrates, solvates and prodrugs thereof is administered topically.

In some embodiments, a topical pharmaceutical composition is applied to specific areas of the anal sphincter, vaginal opening, and/or specific areas of trigger pointed tissue in the pelvic floor muscles of the patient. In some embodiments, the topical pharmaceutical composition is applied using a pressure applicator device, which is inserted into the rectal cavity or vaginal cavity of a human patient through the anal sphincter or vaginal opening and is used to apply a topical pharmaceutical composition. The pressure applicator device is inserted beyond the internal anal sphincter or inside the vagina to a distance where a finger cannot typically reach and pressure is applied at an internal trigger point within the rectal cavity or the vaginal cavity with the pressure applicator device to apply the topical pharmaceutical composition. In addition to treatment by a professional therapist, this also allows for patient self-treatment, enabling a patient with no access to a pelvic floor specialist to self-administer treatment.

In some embodiments, the application of topical pharmaceutical compositions is assisted by the use of a drug applicator sleeve. This sleeve fits around the pressure applicator and allows the patient or therapist to apply compositions directly to the point of pressure application within the vaginal or rectal cavity.

In some embodiments, the methods of the invention involve oral, topical or injectable administration of the calcium channel blocker, or L-arginine, or a combination of a calcium channel blocker and L-arginine, or pharmaceutically acceptable salts, hydrates, solvates and prodrugs thereof, optionally together with a corticosteroid and/or an anesthetic.

In a further aspect, the invention provides methods for relieving muscle soreness or pain comprising applying to the muscle a topical composition comprising a calcium channel blocker, or a pharmaceutically acceptable salt, hydrate, solvate or prodrug thereof.

In a further aspect, the invention provides methods for relieving one or more symptoms of carpal tunnel syndrome, comprising administering a pharmaceutical composition comprising a calcium channel blocker, or a pharmaceutically acceptable salt, hydrate, solvate or prodrug thereof.

BRIEF DESCRIPTION OF THE DRAWINGS

The description herein makes reference to the accompanying drawings, wherein like reference numerals refer to like parts throughout the several views, and wherein:

FIG. 1A is an illustration showing a first example drug delivery device and a pressure applicator in a first position;

FIG. 1B is an illustration showing the first example drug delivery device and the pressure applicator in a second position;

FIG. 2 is an illustration showing a second example drug delivery device;

FIG. 3 is an illustration showing a third example drug delivery device;

FIG. 4 is an illustration showing a fourth example drug delivery device;

FIG. 6A is an illustration showing a sixth example drug delivery device and the pressure applicator in a first position;

FIG. 6B is an illustration showing the sixth example drug delivery device and the pressure applicator in a second position;

FIG. 7A is an illustration showing a seventh example drug delivery device and the pressure applicator in a first position; and FIG. 7B is an illustration showing the seventh example drug delivery device and the pressure applicator in a second position.

FIG. 8A is an illustration showing an embodiment of the drug applicator sleeve of the invention; and FIGS. 8B, 8C and 8D are illustrations showing further embodiments of the drug applicator sleeve of the invention.

DETAILED DESCRIPTION

Figure 5A:
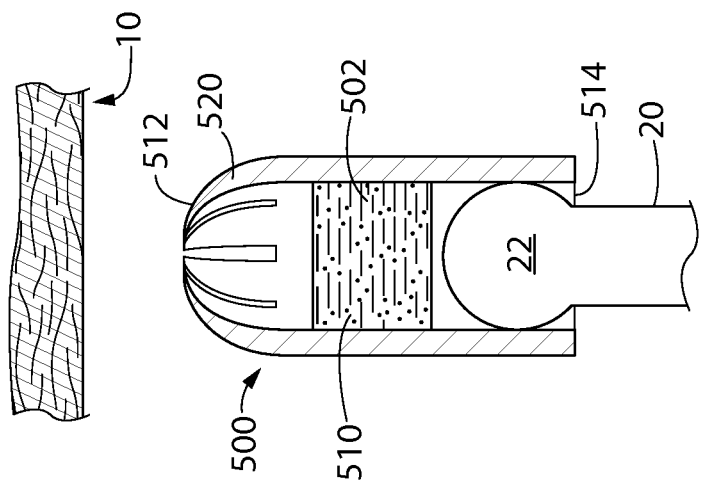
FIG. 5A is an illustration showing a fifth example drug delivery device and the pressure applicator in a first position.

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

As used herein, the term "active agent" or "active ingredient" is intended to mean a calcium channel blocker as described herein, or L-arginine, or a combination of a calcium channel blocker and L-arginine, or pharmaceutically acceptable salts, hydrates, solvates and prodrugs thereof. In some embodiments, the active agent or active ingredient optionally also can include a corticosteroid, for example cortisone or hydrocortisone (cortisol), for management of inflammation. The active agent can be administered to a patient in any pharmaceutically acceptable and effective form, for example by injection or topically via creams, gels, ointments, emulsions, solutions, lotions, suspensions, tinctures, pastes, foams, aerosols, irrigations, sprays, suppositories, or any other formulations or pharmaceutical compositions suitable for topical administration; or orally via any formulation or pharmaceutical composition suitable for oral administration, such as tablets, pills, capsules, and the like.

As used herein, reference to specific types of compounds, for example calcium channel blockers, and specific compounds, for example nifedipine, diltiazem and L-arginine, are intended to include pharmaceutically acceptable salts, hydrates, solvates and prodrugs thereof.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 183-226; specifically 202-205 in *Polymorphism in Pharmaceutical Solids*, (Brittain, H. ed.), Marcel Dekker, Inc., New York, N.Y., 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-Ray diffraction, X-Ray powder diffraction, Polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (http://www.holodiag.com).

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the calcium channel blocker or L-arginine in a preventative fashion. The application of a therapeutic for preventing or prevention of a disease of disorder is known as 'prophylaxis.' In some embodiments, the calcium channel blocker or L-arginine provided herein provide superior prophylaxis because of lower long term side effects over long time periods.

"Prodrug" refers to a derivative of a calcium channel blocker or L-arginine precursor that requires a transformation within the body to release the active drug. Prodrugs are frequently (though not necessarily) pharmacologically inactive until converted to the parent drug.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. In some embodiments, the salts are pharmaceutically acceptable.

"Solvates" refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 183-226; specifically 205-208 in *Polymorphism in Pharmaceutical Solids*, (Brittain, H. ed.), Marcel Dekker, Inc., New York, N.Y., 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-Ray diffraction, X-Ray powder diffraction, Polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holodiag.com).

"Patient" refers to a vertebrate, preferably a mammal. Mammals include, but are not limited to, murines, rodents, simians, humans, farm animals, sport animals and pets.

"Treating" or "treatment" of any disease or disorder refers, in some embodiments, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. In a further feature the treatment rendered has lower potential for long-term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

The term "contacting" is intended to mean causing the coming together of the items to be contacted. For example, "contacting" a muscle with a calcium channel blocker in accordance with the methods of the invention would include any action resulting in the physical contact of the calcium channel blocker with the muscle, for example, local (e.g., by injection) topical, or oral administration of the calcium channel blocker to a patient.

The term "administering" and "applying to the patient" as used in connection with the methods of the invention is intended to include oral, injection, and topical modes of introducing the active ingredients of the invention to the body of a patient by, for example, the self treating patient, physician, physical therapist or other appropriate health care provider.

"Therapeutically effective amount" means the amount of a calcium channel blocker or L-arginine or combination thereof that, when administered to or administered by a patient for treating a disease or condition as described herein, is sufficient to effect such treatment for the disease. The "therapeutically effective amount" will vary depending on the calcium channel blocker or L-arginine, the disease and its severity and the age, weight, adsorption, distribution, metabolism and excretion etc., of the patient to be treated.

It has been discovered in accordance with the present invention that the administration of calcium channel blockers, for example diltiazem and nifedepine, or the administration of L-arginine, either alone or in combination with a calcium channel blocker, can treat pain in a variety of diseases, disorders or conditions. While not wishing to be bound by any particular theory, it is believed that such pain, for example pelvic pain, is caused in many instances by chronically trigger pointed or chronically myofascially restricted muscle. Treatment of the affected muscle, and especially the specific trigger points or myofascially restricted areas thereof, with a calcium channel blocker such as nifedipine or diltiazem in accordance with the present invention, can ameliorate the pain condition.

Thus, in one embodiment, the present invention provides methods for reducing or resolving trigger point activity in muscle of a patient in need thereof comprising contacting the muscle with a therapeutically effective amount of a calcium channel blocker, or L-arginine, or a combination of a calcium channel blocker and L-arginine, or pharmaceutically acceptable salts, hydrates, solvates and prodrugs thereof. The calcium channel blocker, L-arginine, or combination thereof administered can be administered to one or more external or internal trigger points of the muscle manually, or using an applicator such as a syringe or an internal trigger point wand as described below, or via oral administration, or via injection.

In some embodiments, the calcium channel blocker, or L-arginine, or a combination of calcium channel blocker and L-arginine, is administered in a topical formulation intrarectally. As discussed below, such intrarectal administration involves placement of the topical formulation either with an anal syringe, suppository or with a finger up to and slightly past the internal anal sphincter, and also includes the placement and application with an internal trigger point wand and optionally a covering that allows for administration of the medication beyond the internal sphincter into the pelvic floor to reach the levator ani, coccygeus, obturator internus, piriformis, and other pelvic floor muscles in pain with chronic pelvic pain related syndromes, as opposed to perirectal administration, which has been used for example for application of topical formulations to anal fissures, and involves placement of a topical formulation within the first 1 cm of the anal canal. See Golfam, F., et al., The Effect of Topical Nifedipine in Treatment of Chronic Anal Fissure, *Acta Medica Iranica*, Vol. 48, No. 5 (2010), p. 295-299.

As described above, the calcium channel blocker, or L-arginine, or a combination of calcium channel blocker and L-arginine, can administered via injection, which is preferably, but not necessarily, an injection directly into, near to or adjacent to one or more specific trigger points in the muscle; for example the pelvic floor muscles, or external muscles such as, for example, the rectus abdominus, gluteal and adductor muscles or quadratus lumborum of the patient. At the present time, drugs such as bupivacaine (markaine), cortisone and botox have been injected into trigger points with little utility. While not wishing to be bound by any particular theory, it is believed that the vasodilative action of the calcium channel blockers, or the action of L-arginine, as described herein, may reduce the pain or deactivate the trigger point. Significantly, the use of calcium channel blockers as described herein may possess the advantage of not having to be injected directly into a trigger point, but rather injected in the area adjacent to the trigger point, with the result that the vasodilation and relaxation of the specific area may deactivate the trigger points.

Thus, the methods of the invention find use in treating a variety of diseases, disorders and pain conditions including pelvic pain disorders, such as prostatitis category IIIA and/or IIIB in a male patient, chronic pelvic pain, pelvic floor muscles with trigger points or areas of myofascial restriction, chronic pelvic pain syndrome, pelvic floor myalgia, pelvic floor dysfunction, interstitial cystitis, levator ani syndrome, coccygodynia, prostatodynia, prostadynia, piriformis syndrome, anal sphincter pain, bowel movement pain, post bowel movement pain, ejaculatory pain, ejaculatory discomfort, post ejaculatory pain, sitting pain, rectal pain, tailbone pain, urinary frequency, urinary urgency, urinary hesitancy, perineal pain, penile pain, vaginismus, anismus, sexual dysfunction, reduced level of ejaculate or reduced penile erection, nonbacterial prostatitis, slow urinary flow, reduced urinary flow, post ejaculatory discomfort, urinary or urethral sphincter spasms and post urinary pain, rectal sphincter spasms, proctalgia fugax, myofascial pain in muscle tissue of a patient who has one or more trigger points in the muscle tissue, and the pain/sensitivity of pelvic floor muscle trigger points and specific areas of myofascial restriction detected upon palpation in a patient.

In some embodiments, the methods comprise orally or topically administering to a patient in need thereof a therapeutically effective amount of a calcium channel blocker, for example nifedipine or diltiazem, or L-arginine, or a combination of a calcium channel blocker and L-arginine, or pharmaceutically acceptable salts, hydrates, solvates and prodrugs thereof.

In some preferred embodiments, the calcium channel blocker, L-arginine or combination of calcium channel blocker, and L-arginine is applied locally in a topical formulation, preferably in an ointment that will minimize systemic spread of the active ingredient(s), and at a concentration that is uniquely effective for treating the pain condition and reducing the likelihood of the calcium channel blocker becoming significantly systemically absorbed. In some embodiments, the calcium channel blocker, L-arginine or combination thereof is applied by using an applicator, for example a syringe, probe or pressure applicator such as an internal trigger point wand, as described below. In some such embodiments, the calcium channel blocker, L-arginine or combination thereof is administered through the use of a drug applicator sleeve that surrounds the syringe, probe or pressure applicator. In some further preferred embodiments, the calcium channel blocker, L-arginine or combination of calcium channel blocker, and L-arginine is administered orally as described below. In still further embodiments, the calcium channel blocker, L-arginine or combination of calcium channel blocker, and L-arginine is administered via injection, preferably at or near the pelvic floor muscle trigger points and/or specific areas of myofascial restriction.

Accordingly, in one aspect, the present application describes methods (Method 1) for treating, reducing, resolving, eliminating, and/or preventing prostatitis category IIIA and/or IIIB in a male patient. In some embodiments, the methods comprise administering to the male patient in need thereof a therapeutically effective amount of a calcium channel blocker, or L-arginine, or a combination of a calcium channel blocker and L-arginine, or pharmaceutically acceptable salts, hydrates, solvates and prodrugs thereof.

In a further aspect, methods are provided for treating, reducing, resolving, eliminating, and/or preventing chronic pelvic pain, pelvic floor muscles containing trigger points and areas of myofascial restriction, chronic pelvic pain syndrome, pelvic floor myalgia, pelvic floor dysfunction, interstitial cystitis, levator ani syndrome, coccygodynia, prostatodynia, prostadynia, piriformis syndrome, anal sphincter pain, bowel movement pain, ejaculatory pain, ejaculatory discomfort, post ejaculatory pain, sitting pain, post bowel movement pain, rectal pain, tailbone pain, urinary frequency, urinary urgency, urinary hesitancy, perineal pain, penile pain, sexual dysfunction, reduced level of ejaculate or reduced penile erection, nonbacterial prostatitis, slow urinary flow, reduced urinary flow, post ejaculatory discomfort, vaginismus, anismus, anal fissures or tear in the anorectal/anal sphincter area, myofascial pain in muscle tissue of a patient who has one or more trigger points in the muscle tissue, or the pain/sensitivity of pelvic floor muscle trigger points and specific areas of myofascial restriction detected upon palpation in a patient. In some embodiments, the methods comprise administering to the patient in need thereof a therapeutically effective amount of a calcium channel blocker, or L-arginine, or a combination of a calcium channel blocker and L-arginine, or pharmaceutically acceptable salts, hydrates, solvates and prodrugs thereof.

Post urinary pain is pain that occurs after urination. While not wishing to be bound by any particular theory, it is believed that the pain can result from spasm in the urinary sphincter, and that administration, preferably oral administration, and even more preferably extended release oral administration, of a calcium channel blocker, for example nifedipine or diltiazem, or a pharmaceutically acceptable salt, hydrate, solvate or prodrug thereof in accordance with the methods of the invention, will treat the condition—i.e., will prevent or reduce the post urinary pain—by reducing the occurrence and/or intensity of spasm in the urinary sphincter.

Proctalgia fugax is a severe, episodic rectal spasm, which can occur at any time, but frequently occurs at night, and sometimes is very distressing and frightening. While not wishing to be bound by any particular theory, it is believed that proctalgia fugax results from spasm in the anal sphincter, rectum, or in the pubococcygeus or levator ani muscles. Thus, it is believed that administration, either oral or topical, preferably oral administration, and even more preferably extended release oral administration, of a calcium channel blocker, for example nifedipine or diltiazem, or a pharmaceutically acceptable salt, hydrate, solvate or prodrug thereof in accordance with the methods of the invention, will treat the condition—i.e., will prevent or reduce the pain—by reducing the occurrence and/or intensity of spasm in the anal sphincter, rectum, or in the pubococcygeus, levator ani muscles, or other pelvic floor muscles through reducing calcium in the calcium channels of the muscles, especially in smooth muscle.

Thus, in some embodiments, the invention provides methods for treating urinary sphincter spasms, urethral sphincter spasms, post urinary pain, rectal sphincter spasms, and proctalgia fugax; which methods preferably comprise topical or oral administration, and preferably extended release oral administration, of a calcium channel blocker, for example nifedipine or diltiazem, or a pharmaceutically acceptable salt, hydrate, solvate or prodrug thereof, to a patient in need of treatment.

In some embodiments, the invention provides methods for treating pain conditions, for example chronic pelvic pain, chronic pelvic pain without fissures or fistulas, chronically trigger pointed pelvic floor muscles, chronic pelvic pain syndrome, pelvic floor myalgia, pelvic floor dysfunction, interstitial cystitis, overactive bladder, levator ani syndrome, coccygodynia, prostatodynia, piriformis syndrome, anal sphincter pain, bowel movement pain, post bowel movement pain, ejaculatory pain, post ejaculatory pain, sitting pain, rectal pain, tailbone pain, urinary frequency, urinary urgency, urinary hesitancy, perineal pain, penile pain, vaginismus, anismus, sexual dysfunction, reduced level of ejaculate or reduced penile erection, myofascial pain in muscle tissue of a patient who has one or more trigger points in the muscle tissue, conditions characterized by muscle spasm or soreness, urinary sphincter spasms, urethral sphincter spasms, post urinary pain, rectal sphincter spasms and proctalgia fugax, or the pain/sensitivity of pelvic floor muscle trigger points and specific areas of myofascial restriction detected upon palpation in a patient, said method comprising use of one or more dilators. The dilator or dilators may include anal, vaginal or urethral dilators, and pediatric dilators. In some embodiments, the aforementioned chronic pelvic pain exists with or without fissures or fistulas or evidence of hypertonus or other pathology in external or internal anal sphincters. In another particular embodiment, the chronic pelvic pain syndrome exists with pain containing or referring to trigger points.

Dilators for use in accordance with the methods of the invention are preferably are preferably sized from ¼ inch in diameter to 1½" inches in diameter, for example in size increments of ¹⁄₁₆ or ⅛ of an inch. In some embodiments, treatment further comprises the progressive transitioning from smaller sized dilators to larger sized dilators. In some preferred embodiments, the methods of the invention comprise the use of the dilators daily, or more than once daily, for example twice daily, three times daily, or more, for a period of time at each instance, for example of from about 10 minute to about 40 minutes, or about 20 minutes to about 30 minutes. The methods of the invention can be employed for a fixed period of time, for example on a single day, for several days, a week, 1 month, or longer. In some embodiments, treatment with the methods of the invention is continued until symptoms are resolved.

The dilators for use in the methods of the invention may be of any suitable shape or design, including any currently available to patients and medical practitioners. The dilators may be made of any suitable material, including but not limited to, synthetic plastics and polymers, such as silicone, and metals. Use of the dilators in accordance with the invention may optionally involve the use of lubricants. The use of dilators in accordance with the methods of the invention can be by the patient, or another, for example and a doctor, physical therapist or other health care professional.

In some embodiments, the methods of the invention comprise the use of dilators as described above, and also include the administration of a calcium channel blocker, or a pharmaceutically acceptable salt thereof, or a pharmaceutical composition thereof, as described herein. The calcium channel blocker may be administered orally (e.g., as an oral composition), for example, in the form of a pill, tablet or capsule. Alternatively, the calcium channel blocker may be administered topically (e.g., as a topical composition), such as an ointment, gel or paste. In some embodiments, the calcium channel blocker, or pharmaceutical composition thereof, may be administered prior to use of the dilator, for example from 5 minutes to 60 minutes prior to dilator use, from 10 minutes to 60 minutes prior to dilator use; from 20 minutes to 60 minutes prior to dilator use; or from 30 to 60 minutes prior to dilator use. In some embodiments, a local anesthetic agent may also be administered concomitantly or sequentially dilator use. Such local anesthetic may also be a component of the pharmaceutical composition containing the calcium channel blocker, for example as in topical compositions as described herein. In some preferred embodiments, the calcium channel blocker used with the dilator is nifedipine.

The use of both the calcium channel blocker, e.g. nifedipine, and the dilator uniquely addresses the problem of pain conditions both mechanically and pharmacologically.

In some embodiments, the invention provides methods for relieving muscle soreness or pain in a patient in need thereof, comprising applying to the muscle a topical composition comprising a calcium channel blocker or a pharmaceutically acceptable salt, hydrate, solvate or prodrug thereof. In some such embodiments, the topical composition is a balm, which can comprise one or more analgesics, fragrances and excipients, for example and not limitation menthol, menthone, camphor, pulegol, isopulegol, cin eole, mint oil, peppermint oil, spearmint oil, eucalyptus oil, 3-(1-menthoxy)propane-1,2-diol, N-alkyl-p-menthane-3-carboxamide, 2-methyl-3-(1-menthoxy)propane-1,2-diol, p-menthane-3,8-diol, 2-(1-menthoxy)ethan-1-ol, 3-(1-menthoxy)propan-1-ol, 4-(1-menthoxy)butan-1-ol, menthyl 3-hydroxybutanoate, menthyl lactate, menthone glycerin ketal, N-methyl-2,2-isopropylmethyl-3-methylbutane amide, menthyl glyoxylate cajuput oil, clove oil, dementholized mint oil and paraffin petrolatum. Typically, balms are applied and massaged into the intended muscle.

Carpal Tunnel Syndrome (CTS) is a median entrapment neuropathy that causes paresthesia, pain, numbness, and other symptoms in the distribution of the median nerve due to its compression at the wrist in the carpal tunnel. The main symptom of CTS is intermittent numbness of the thumb, index, long and radial half of the ring finger. Long-standing CTS leads to permanent nerve damage with constant numbness, atrophy of some of the muscles of the thenar eminence, and weakness of palmar abduction.

In some embodiments, the present invention provides methods for relieving one or more symptoms of carpal tunnel syndrome in a patient in need thereof, comprising administering to a patient in need thereof a pharmaceutical composition comprising a calcium channel blocker, or a pharmaceutically acceptable salt, hydrate, solvate or prodrug thereof. In some such embodiments, a topical composition as described herein is applied to the muscle. In other such embodiments, an oral pharmaceutical composition as described herein is administered. While not wishing to be bound by any particular theory, it is believed that vasodilative action of the calcium channel blockers may reduce the pain and soreness in muscle, and also reduce, for example, numbness and pain in patients suffering from carpal tunnel syndrome.

Overactive bladder is a urinary storage dysfunction that causes a sudden urge to urinate. Symptoms can include frequent urination, frequent interruptions of sleep due to the need to urinate (nocturia), and urinating unintentionally followed by an urge to continue (urge incontinence). In some embodiments, the present invention provides methods for relieving one or more symptoms of overactive bladder, comprising administering to a patient in need thereof a pharmaceutical composition comprising a calcium channel blocker, or a pharmaceutically acceptable salt, hydrate, solvate or prodrug thereof. While not wishing to be bound by any particular theory, it is believed that overactive bladder in many cases is in fact a symptom of pelvic floor dysfunction, and that the present methods described herein will find use in effectively ameliorating the symptoms of overactive bladder.

Vaginismus is a condition in which an involuntary vaginal muscle spasm makes any kind of vaginal penetration painful or impossible. Anismus refers to the failure of the normal relaxation of pelvic floor muscles during attempted defecation. While not wishing to be bound by any particular theory, it is believed that the use calcium channel blockers in accordance with the invention will result in relaxation and/or reduction in tone of the pubococcygeus muscle, or other potentially affected muscles such as the bulbocavernosus, circumvaginal, and perivaginal muscles (in the case of vaginismus) and pelvic floor muscles (in the case of anismus), to relieve the symptoms of these conditions While not wishing to be bound by any particular theory, it is thought that while the calcium channel blockers act most directly on smooth muscle to reduce tone and trigger point activity, the application of nifedipine or other calcium channel blockers orally or topically may reduce the tone, trigger point activity and myofascial restriction of smooth muscle found, in around and adjacent to the striated muscles in the pelvic floor.

For treatment of vaginismus or anismus with topical calcium channel blocker in accordance with the invention, it is generally preferred to apply the calcium channel blocker vaginally for vaginismus, or perianally or intrarectally for anismus. In some embodiments, this can be accomplished by using a finger or an applicator. Effectiveness can be measured by anal manometry, as well as the report of the patient of functioning of the anus and/or vagina in defecation, sexual activity, sitting and general levels of pain/discomfort.

Calcium channel blockers are a class of drugs that selectively inhibit calcium movement through calcium channels in cell membranes. Accordingly, calcium channel blockers have a number of physiological effects including, for example, reduction of hypertension.

Since their discovery in 1964, a wide variety of calcium channel blockers have been characterized, any of which can be used in the present invention. Calcium channel blockers are typically divided into several classes of compounds, including but are not limited to, dihydropyridines, phenylalkylamines, benzothiapenes, zicotonide, or non-selective compounds. Exemplary dihydropyridine calcium channel blockers for use in the present invention include, but are not limited to, amlopidine, aranidipine, azelnidipine, barnidipine, benidipine, cilnidipine, clevidipine, isradipine, efonidipine, felodipine, lacidipone, lercanidipine, manidipine, nicardipine, nifedipine, nilvadipine, nimodipine, nisoldipine, nitrendipine or pranidipine. In some embodiments, the dihydropyridine calcium channel blocker is nifedipine. Typical phenylalkylamine calcium channel blockers include, but are not limited to varapamil, gallopamil or fendiline. An exemplary benzothiazepine calcium channel blocker is, for example, diltiazem, while typical non-selective calcium channel blockers include, but are not limited to, mibefradil, bepridil, flunarizine, fluspirilene or fendiline. In some embodiments, the calcium channel blocker is diltiazem or nifedipine.

L-Arginine (Arg) is a conditionally essential amino acid, naturally found in dietary protein. It is converted to nitric oxide (NO) and bronchodilator, a potent vasodilator, by a family of enzymes known as nitric oxide synthase (NOS). NO is an essential molecule that plays a role in a broad range of functions from vascular regulation, neurotransmission, host defense, and cytotoxicity to physiologic control of airways. Recently, L-arginine has gained popularity as a dietary supplement, and has been reported to be useful for treatment of anal fissures (Gosselink, M. P. et al., Dis. Colon Rectum. 2005 48(4): 832-837).

Corticosteroids are known to be useful for, inter alia, treating acute inflammation. In some embodiments of the methods of the invention as described herein, the pharmaceutical compositions of the invention include, in addition to the therapeutically effective amount of a calcium channel blocker, or L-arginine, or a combination of a calcium channel blocker and L-arginine, or pharmaceutically acceptable salts, hydrates, solvates and prodrugs thereof, a corticosteroid, for example cortisone or hydrocortisone. While not wishing to be bound by any particular theory, it is believed that the inclusion of the corticosteroid will assist in alleviating inflammation, and the calcium channel blocker will promote vasodilation and relaxation of the muscle to which the pharmaceutical composition is administered or applied. Suitable corticosteroids include 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone diacetonide, and triamcinolone hexacetonide; and a pharmaceutically acceptable salts thereof, or phosphate prodrugs thereof, or ester prodrugs thereof.

Pharmaceutical Compositions

The pharmaceutical compositions provided herein contain therapeutically effective amounts of one or more of compounds provided herein that are useful in the treating, reducing, resolving, eliminating, ameliorating and/or preventing the conditions described herein, or one or more of the symptoms thereof. The pharmaceutical compositions comprise a calcium channel blocker, or L-arginine, or a combination of a calcium channel blocker and L-arginine, or pharmaceutically acceptable salts, hydrates, solvates and prodrugs thereof in a pharmaceutically acceptable vehicle, carrier, diluent, or excipient, or a mixture thereof.

In one embodiment, provided herein are pharmaceutical compositions in modified release dosage forms, which comprise a calcium channel blocker, or L-arginine, or a combination of a calcium channel blocker and L-arginine, or pharmaceutically acceptable salts, hydrates, solvates and prodrugs thereof, and one or more release controlling excipients as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions may also comprise non-release controlling excipients.

Further provided herein are pharmaceutical compositions in enteric coated dosage forms, which comprise a calcium channel blocker, or L-arginine, or a combination of a calcium channel blocker and L-arginine, or pharmaceutically acceptable salts, hydrates, solvates and prodrugs thereof, and one or more release controlling excipients for use in an enteric coated dosage form. The pharmaceutical compositions may also comprise non-release controlling excipients.

Additionally provided are pharmaceutical compositions in a dosage form that has an instant releasing component and at least one delayed releasing component, and is capable of giving a discontinuous release of the active ingredient(s) in the form of at least two consecutive pulses separated in time from 0.1 up to 24 hours. The pharmaceutical compositions comprise a calcium channel blocker, or L-arginine, or a combination of a calcium channel blocker and L-arginine, or pharmaceutically acceptable salts, hydrates, solvates and prodrugs thereof, and one or more release controlling and non-release controlling excipients, such as those excipients suitable for a disruptable semi-permeable membrane and as swellable substances.

In certain embodiments, provided herein are pharmaceutical compositions in a dosage form for oral administration to a subject, which comprise a calcium channel blocker, or L-arginine, or a combination of a calcium channel blocker and L-arginine, or pharmaceutically acceptable salts, hydrates, solvates and prodrugs thereof, and one or more pharmaceutically acceptable excipients or carriers, enclosed in an intermediate release layer or matrix material, and an enteric coating.

In one embodiment, the pharmaceutical compositions herein may be provided in unit-dosage forms or multiple-dosage forms. Unit-dosage forms, as used herein, refer to physically discrete units suitable for administration to human and animal subjects and packaged individually as is known in the art. Each unit dose contains a predetermined quantity of the active ingredient(s) sufficient to produce the desired therapeutic effect, in association with the required pharmaceutical carriers or excipients. Examples of unit dosage forms include ampoules, syringes including anal syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, and the like.

The calcium channel blocker, or L-arginine, or a combination of a calcium channel blocker and L-arginine, or pharmaceutically acceptable salts, hydrates, solvates and prodrugs thereof provided herein may be administered alone, or in combination with one or more other compounds provided herein, one or more other active ingredients. The pharmaceutical compositions that comprise a calcium channel blocker, or L-arginine, or a combination of a calcium channel blocker and L-arginine, or pharmaceutically acceptable salts, hydrates, solvates and prodrugs thereof provided herein may be formulated in various dosage forms for oral, parenteral, and topical administration. The pharmaceutical compositions may also be formulated as modified release dosage forms, including delayed-, extended-, prolonged-, sustained-, pulsatile-, controlled-, accelerated- and fast-, targeted-, programmed-release, and gastric retention dosage forms. Modified or sustained release agents include polymers such as the Eudragit® series and cellulose esters. These dosage forms can be prepared according to conventional methods and techniques known to those skilled in the art (see, Remington: The Science and Practice of Pharmacy, supra; Modified-Release Drug Deliver Technology, Rathbone et al, Eds., Drugs and the Pharmaceutical Science, Marcel Dekker, Inc.: New York, N.Y., 2002; Vol. 126).

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

The active materials can also be mixed with other active materials which do not impair the desired action, or with materials that supplement the desired action, such as antacids, H2 blockers, and diuretics. The active ingredient is a compound or derivative thereof as described herein. Higher concentrations, up to about 98% by weight of the active ingredient may be included.

Oral Administration

The pharmaceutical compositions provided herein may be provided in solid, semisolid, or liquid dosage forms for oral administration. Suitable oral dosage forms include, but are not limited to, tablets, capsules, pills, troches, pellets, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, enteric coatings, film costing agents, modified release agents, coloring agents, dye-migration inhibitors, sweetening agents, and flavoring agents.

Binders or granulators impart cohesiveness to a tablet to ensure that the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, ethylcellulose, carboxymethylcellulose, methylcellulose, methyl paraben, polyalkyleneoxides, povidone, polyvinylpyrrolidone (PVP), crospovidones, Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxy ethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, trehalose, lysine, leucine, lecithin, starch, kaolin, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms. Thus, in some preferred embodiments, the active ingredient(s) (i.e., the calcium channel blocker, or L-arginine, or a combination of a calcium channel blocker and L-arginine, or pharmaceutically acceptable salts, hydrates, solvates and prodrugs thereof), is administered in a pharmaceutical composition which is an immediate release oral dosage form, preferably but not necessarily including an enteric coating. In some preferred embodiments, the active ingredients(s) are administered in a pharmaceutical composition which is an extended release oral dosage form, preferably but not necessarily including an enteric coating. In further preferred embodiments, the active ingredients are administered in a pharmaceutical composition which contains both an immediate release dose and an extended release dose or pulsed release dose of the calcium channel blocker, preferably but not necessarily also including an enteric coating. Such dual release dosage forms achieve release of an initial dose of active ingredient, followed late in time by another pulsed release, or by a sustained release dose. Methodologies for preparing such dual release dosage forms are well known in the art.

In some embodiments, the active ingredients are formulated into a controlled release matrix tablet, which contains one or more polymeric matrix materials that promote the sustained, delayed or pulsed release profile. Non-limiting examples of such polymeric matrix materials include cellulosic materials as described above, and carbomers, for example those sold by Lubrizol Corporation under the name Carbopol®, for example Carbopol® 71G NF, Carbopol® 971P NF and Carbopol® 974P NF polymers.

Some preferred examples of extended release compositions suitable for use in the methods and compositions of the invention include, for example and not limitation, extended release compositions found in nifedipine formulations such as Adalat CC®, Procardia® XL, Afeditab® CR and Nifedical® XL; and in diltiazem formulations such as Cardizem® CD, Cardizem® LA, Cardizem® SR, Cartia® XT and Dilacor® XR.

Oral administration of the calcium channel blocker, or L-arginine, or combination of a calcium channel blocker and L-arginine, or pharmaceutically acceptable salts, hydrates, solvates and prodrugs thereof, with or without an anti-inflammatory active such as cortisone or cortisol, is particularly effective for patients that have conditions that limit direct access to the target muscle, e.g., patients that suffer from, for example and not limitation, anal cancer and patients who have had a colostomy. The sphincters of these patients are typically sewn shut, thus limiting the direct rectal access to the pelvic floor muscles. It should be noted that while oral administration in accordance with the methods of the invention is particularly indicated for such patients, oral administration is also a particularly convenient route of administration for all patients, including those with direct access to the target muscle.

In some embodiments, the invention provides pharmaceutical compositions for oral administration, and particularly extended release oral formulations, for use in treating the conditions and disorders described herein, including for example pelvic pain disorders, such as prostatitis category IIIA and/or IIIB in a male patient, chronic pelvic pain, pelvic floor muscles with trigger points or areas of myofascial restriction, chronic pelvic pain syndrome, pelvic floor myalgia, pelvic floor dysfunction, interstitial cystitis, levator ani syndrome, coccygodynia, prostatodynia, prostadynia, piriformis syndrome, anal sphincter pain, bowel movement pain, post bowel movement pain, ejaculatory pain, ejaculatory discomfort, post ejaculatory pain, sitting pain, rectal pain, tailbone pain, urinary frequency, urinary urgency, urinary hesitancy, perineal pain, penile pain, vaginismus, anismus, sexual dysfunction, reduced level of ejaculate or reduced penile erection, nonbacterial prostatitis, slow urinary flow, reduced urinary flow, post ejaculatory discomfort, urinary or urethral sphincter spasms, post urinary pain, rectal sphincter spasms, proctalgia fugax, myofascial pain in muscle tissue of a patient who has one or more trigger points in the muscle tissue, and the pain/sensitivity of pelvic floor muscle trigger points and specific areas of myofascial restriction detected upon palpation in a patient; wherein the composition comprises a calcium channel blocker, for example nifedipine or diltiazem. In some embodiments, the calcium channel blocker is nifedipine, which is present in an amount of from 1-90 mg. In some further embodiments, the calcium channel blocker is nifedipine, which is present in an amount of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 mg of nifedipine; preferably 5, 10, 15, 20, 25, 30, 35, 40, 45, 50, 55, 60, 65, 70, 75, 80, 85 or 90 mg of nifedipine, or 5, 15, 25, 35, 40, 45, 50, 55, 65, 70, 75, 80, 85 or 90 mg of nifedipine. In some preferred embodiments, the pharmaceutical composition is an extended release composition.

In some embodiments, the methods of the invention include the administration of an enterically coated extended release dosage form comprising calcium channel blocker as described herein, for example nifedipine or diltiazem, wherein the calcium channel blocker is embedded within, or encapsulated by, one or more mucoadhesive polymers. Preferably, the mucoadhesive polymer(s) has extended release properties—i.e., it effects a delayed release of active from the polymer—or the dosage form additionally contains one or more delay-released agents, as described below, to effect a delayed release of the active(s). In some such embodiments the enteric coating delays release of the mucoadhesive polymer containing the active ingredient(s) until the dosage form is in the large intestine. While not wishing to be bound by a particular theory, it is believed that upon release or shortly thereafter, the mucoadhesive polymer will adhere to the wall of the large intestine, and the active ingredients will then be released slowly to the local environment, where it will both exert its effect locally, and also diffuse into the blood. Thus, it is thus believed that the release and distribution profile of the dosage form will display both systemic and local effects. It is believed that such a dual effect would aid in lessening the spasticity of the affected muscles, for example colon muscles and pelvic floor muscles, and thus afford significant benefits in treatment of the conditions described herein, including anal fissures, pelvic pain disorders, chronic pelvic pain, pelvic floor muscles with trigger points or areas of myofascial restriction, chronic pelvic pain syndrome, pelvic floor myalgia, pelvic floor dysfunction, interstitial cystitis, levator ani syndrome, coccygodynia, prostatodynia, prostadynia, piriformis syndrome, anal sphincter pain, bowel movement pain, post bowel movement pain, ejaculatory pain, ejaculatory discomfort, post ejaculatory pain, sitting pain, rectal pain, tailbone pain, urinary frequency, urinary urgency, urinary hesitancy, perineal pain, penile pain, vaginismus, anismus, sexual dysfunction, reduced level of ejaculate or reduced penile erection, nonbacterial prostatitis, slow urinary flow, reduced urinary flow, post ejaculatory discomfort, urinary or urethral sphincter spasms, post urinary pain, rectal sphincter spasms, proctalgia fugax, myofascial pain in muscle tissue of a patient who has one or more trigger points in the muscle tissue, and the pain/sensitivity of pelvic floor muscle trigger points and specific areas of myofascial restriction detected upon palpation in a patient.

Suitable mucoadhesive polymers include, but are not limited to, natural, semi-synthetic and synthetic polymers, hydrophilic polymers, hydrogels, protein polymers (proteins and polypeptides), carbohydrate polymers (polysaccharides), glycoproteins, copolymers including block copolymers, and any of the foregoing that have been further modified to include thiol or disulfide functional groups (thiolated polymers). Such thiolated polymers may include modifications of natural, semi-synthetic or synthetic polymers that incorporate cysteine, homocysteine, thioglycolic acid, thioethylamidine, iminothiolane, isonicotinamide-disulfide, pyridoxine-dilsulfide, or other thiol or disulfide functional groups. Natural polymers include, but are not limited to, alginates, agarose, pectins, chitosans, mucins, gelatin, gums (e.g., guar gum, karaya gum, xanthan gum, Arabic gum, gellan gum, carrageenan), retene, tragacanth, hyaluronan, starches and celluloses. Semi-synthetic polymers include any natural polymers modified by chemical or physical means. Further suitable mucoadhesive polymers include those that are modified to incorporate specific bacterial fimbrial proteins, such as *E. Coli* antigen K99. Specific nonlimiting examples of mucoadhesive polymers embraced by the current invention include cellulose, microcrystalline cellulose, modified celluloses (including hydroxypropyl methylcellulose, hypromellose, hydroxyethyl cellulose, hydroxypropyl cellulose, hydroxymethyl cellulose, sodium carboxymethyl cellulose and ethyl cellulose), poly(vinylpolypyrrolidone) (Crospovidone), poly(vinylpyrrolidone) (Povidone), polydextrose, polyvinyl alcohol, polysorbate, polyethylene glycol, polyethylene oxide (including Polyox WSR), polyacrylic acid, polypropylene glycol, polyethylene glycol/polypropylene glycol block copolymers (such as Poloxamers, including Poloxamer 407P and Poloxamer 188P), cross-linked polyacrylates (such as Carbopols, including Carbopol 934P, Carbopol 940, Carbopol 971P, Carbopol 974P, Carbopol 981), cyclodextrins (including alpha-, beta- or gamma-cyclodextrin, and modified cyclodextrins such as hydroxypropyl-beta-cyclodextrin), dextrans, dendrimers, polycarbophil, poly(dimethyl siloxane), poly(hydroxyethyl methacrylate), cyanoacrylates, hyaluronic acid, polyvinyl ethers, wheat germ agglutinin, and natural-synthetic polymer complexes (such as poly(ethylene glycol)-alginate complex). Further examples are disclosed in Shaikh, et al., Mucoadhesive Drug Delivery Systems, J. Pharm. Bioallied Sci., 2011 January-March, 3(1):89-100, and the references cited within, which is incorporated herein by reference in its entirety.

In some embodiments of the methods of the invention, an oral dose of a calcium channel blocker, for example nifedipine or diltiazem, is administered in conjunction with the protocol involving manual or device-assisted placement of a topical pharmaceutical composition, for example by use of a trigger-point wand, as discussed above. While not wishing to be bound by a particular theory, it is believed that the oral calcium channel blocker facilitates the usefulness of the protocol by relaxing the anal sphincter, and thus affording easier, less painful and more effective use of the protocol.

Parenteral Administration

The present invention also includes parenteral administration, in particular by injection, preferably directly into muscle of a patient, more preferably directly into to one or more specific trigger points in the muscle, for example and not limitation, the pelvic floor muscle, or external trigger pointed muscle.

The pharmaceutical compositions provided herein may be administered parenterally by injection, infusion, or implantation, preferably but not necessarily for local administration. Parenteral administration, as used herein, includes intramuscular and subcutaneous administration, and includes the administration of long-acting or depot intramuscular drug formulations.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

Pharmaceutical compositions suitable for injection can be prepared in conventional forms, either as liquid solutions or suspensions, solid forms suitable for solution or suspension in liquid prior to injection, or as emulsions. The compositions also can contain one or more excipients such as, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Injectable pharmaceutical compositions also can other components known to be useful in injectable formulations, and in particular intramuscular injection formulations, for example isotonic agents such as sodium chloride and dextrose, buffers such as phosphate and citrate; antioxidants such as sodium bisulfate; local anesthetics such as lidocaine and procaine hydrochloride; suspending and dispersing agents such as sodium carboxymethylcelluose, hydroxypropyl methylcellulose and polyvinylpyrrolidone; and emulsifying agents such as Polysorbate 80 (Tween® 80).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propylparabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including alpha-cyclodextrin, beta-cyclodextrin, hydroxypropyl-beta-cyclodextrin, sulfobutylether-beta-cyclodextrin, and sulfobutylether 7-beta-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Lyophilized powders, which can be reconstituted for administration as solutions, emulsions and other mixtures, or reconstituted and formulated as solids or gels, also find use with the present invention. The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbital, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration as described above. For reconstitution, the lyophilized powder is added to sterile water or other suitable carrier. The precise amount depends upon the selected compound. Such amount can be empirically determined.

Generally, the concentration of active agent is adjusted so that an injection provides an effective amount to produce the desired pharmacological effect in the affected muscle. Injectables in accordance with the invention are preferably designed for local administration, and preferably avoid systemic administration of the active agent. The exact dose depends on the specific condition of the patient or animal as is known in the art.

Topical Administration

The topical pharmaceutical compositions provided herein may be administered to the skin, orifices, or mucosa. The topical administration, as used herein, includes (intra)dermal, transdermal, vaginal, uretheral, and rectal and intrarectal administration. Topical formulations may include from 0.5 to 5% calcium channel blocker, for example 0.5 to 3% nifedipine.

In some embodiments, administration of the active ingredients of the invention differs from current treatment of open wounds such as anal fissures. For example, topical treatment of anal fissures typically involves administration of a topical formulation to an area between the anal opening and the first 1 cm of the anal canal (see, for example, Golfam, F., et al., supra), and in some cases to approximately the first 1 to 3.5 inches of the anal canal. In contrast, the trigger points typically identified in accordance with the conditions identified herein are typically in the internal and external anal sphincter and located in the muscles of the pelvic floor as illustrated and described in the $6^{th}$ edition of Wise's book, A Headache in the Pelvis, described supra. While not wishing to be bound by any particular theory, it is believed that tissue and environmental differences between the two sites can influence the permeability and effectiveness of the applied composition.

In addition, the present invention also provides compositions and methods for treatment of anal fissures, and alleviation of symptoms of anal fissures, which in one embodiment comprises perianal or intrarectal administration of a topical composition comprising the active ingredients according to the present invention, and in a further embodiment comprises oral administration of the active ingredients according to the present invention, each to a patient in need thereof.

In some preferred embodiments, the methods of the invention are performed using topical pharmaceutical compositions as described herein. For topical compositions in accordance with the invention, administration is preferably local. In some preferred embodiments, a topical pharmaceutical composition is prepared for local administration and specifically avoids systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration. The mixture may include glycerin or a poloxamer, paraffin, conventional ointment formulations or any other suitable material. The topical pharmaceutical composition may include a local anesthetic such as, for example, benzocaine, chloroprocaine, cocaine, cyclomethycaine, lidocaine, dimethococaine, piperocaine, procaine, novocaine, procaine, tetracaine, articane, bupivacaine, cinchocaine, dibucaine, etidocaine, levobupivicanine, lignocaine, mepivocaine, prilocaine, ropivacaine, trimecaine, eugenol, menthol, saxitoxin or tetrodoxin. In some embodiments, the local anesthetic is lidocaine.

In still other embodiments, the topical pharmaceutical composition may contain 1.5% lidocaine. In some embodiments, a topical pharmaceutical composition includes 2% diltiazem, 1.5% lidocaine, in a base of 30% poloxamer 407 and glycerin or in a paraffin or ointment base of any typical kind. In some embodiments, a topical pharmaceutical composition includes 0.3%-3% nifedipine, in 30% poloxamer 407 and/or in a paraffin or ointment base of any typical kind. In some embodiments, a topical pharmaceutical composition includes 0.5%-1% nifedipine, in a base of any typical kind.

In some embodiments, the topical pharmaceutical composition is applied by use of a protocol involving manual or device-assisted placement of a topical pharmaceutical composition, as discussed below.

In some embodiments, the topical pharmaceutical composition is applied by placing the medication on one's gloved finger to then be inserted inside the sphincter or vagina as far as a finger can reach to places where trigger points reside that the patient has been taught to locate and to apply the calcium channel blocker topically. In some embodiments, the topical pharmaceutical composition is applied by placing the medication on the tip of a device to then be inserted inside the sphincter or vagina. Examples of devices that are suitable for this purpose are internal trigger point wands (see, e.g. U.S. Pat. Nos. 8,337,435 and 8,224,464, each of which is incorporated herein by reference in its entirety for all purposes). In some embodiments, the topical pharmaceutical composition is applied by the use of a drug applicator sleeve and in combination with a device such as, for example, a syringe, probe or pressure applicator such as an internal trigger point wand, as described below. In some such embodiments, the calcium channel blocker, L-arginine or combination thereof is administered through the use of a drug applicator sleeve that surrounds the syringe, probe or pressure applicator.

In some preferred embodiments, the topical pharmaceutical composition is applied to identified trigger points as described herein. Procedures for identifying such trigger points are known, and within the ambit of this of skill in the art. Typically, a skilled practitioner will take a history of a patient complaining of pain and will know the approximate number and location of trigger points associated with the symptom that is being complained of. The skilled practitioner who treats pelvic pain will then palpate tissue both outside and inside of the pelvic floor to see if the typical indications of a trigger point (jump sign upon palpation, twitch response felt by practitioner upon palpation, perception of a taut band of muscle fiber that is exquisitely tender and refers pain and typically recreates the symptom of the patient). The foregoing procedures are also described in Travell & Simons, *Myofascial Pain and Dysfunction, The Trigger Point Manual* (*Volumes I and II*), $2^{nd}$ Ed., J. Butler, Ed., Williams & Wilkins; 1983. See also Wise, D. T. et al., A Headache in the Pelvis: A new understanding and treatment for chronic pelvic pain syndromes, $6^{th}$ ed.; ISBN 978-0-9727755-5-7; National Center for Pelvic Pain Research, PO Box 54, Occidental, Calif. 95465; pp. 104-110: 265-277; 379-387: Anderson et al., Painful Myofascial Trigger Points and Pain Sites in Men With Chronic Prostatitis/Chronic Pelvic Pain Syndrome, *J Urol* 182 (6): 2753-8, each of which is incorporated by reference in its entirety.

Preferably, the topical pharmaceutical composition is a cream or ointment, which can be, but is not necessarily, sticky and thickening with body heat—i.e., will tend to stick to the tissue to which it is applied. While not wishing to be bound by any particular theory, it is believed that a sticky ointment might promote local administration and efficacy of the active ingredient(s) by preventing migration of the ointment to other tissues. Moreover, it is preferable that the topical composition possesses a suitable balance between gel and liquid properties. It has been found that such properties are successfully imparted by inclusion of a nonionic surfactant with glycerin or in a paraffin or ointment base of any typical kind. In one preferred embodiment, the topical pharmaceutical composition comprises a poloxamer, for example poloxamer 407®. While not wishing to be bound by any particular theory, it is believed that poloxamers, and in particular poloxamer 407® are advantageous in that the combination of the poloxamer plus calcium channel blocker, for example and not limitation nifedipine or diltiazem, and/or L-arginine, forms a unique composition that has bioadhesive and healing properties. It also is believed that the composition has the beneficial property of increasing in viscosity or solidity as its temperature increases. These properties may be beneficial in promoting the local administration of the active ingredient(s), and resisting systemic absorption. Indeed, in the methodology discussed in the Wise publications mentioned above, patients are taught the anatomy of pelvic floor, and the application of pressure in specific areas in the pelvic floor to relieve trigger point activity, either manually or using an applicator such as a syringe or an internal trigger point wand as described in, e.g. U.S. Pat. Nos. 8,337,435 and 8,224,464, each of which is incorporated herein by reference in its entirety for all purposes. In some embodiments of the present invention, the patient uses the wand to deliver a bioadhesive product of the invention; e.g., a composition comprising poloxamer 407® and a calcium channel blocker, L-arginine, or both, to the specific area. It is believed that the bioadhesive properties of the composition retards migration of the composition, thus promoting the retention of active ingredients in the specific place it is most effective, and thus also minimizing systemic absorption.

Thus, in some embodiments, the pharmaceutical compositions of the invention can include one or more mucoadhesive polymers, which serve to prolong the residence time of the dosage form through various mucosal routes in drug delivery applications, and enhance bioavailability of the active ingredient(s). Examples of mucoadhesive polymers include, without limitation, the cellulose derivatives discussed above, poly(acrylic acids) such as Carbopol® polymers, also described above, and Gantrez® copolymers such as poly(methylvinylether/maleic anhydride). Further examples are disclosed in Shaikh, et al., Mucoadhesive Drug Delivery Systems, J. Pharm. Bioallied Sci., 2011 January-March, 3(1):89-100, and the references cited within.

Preferred nonionic surfactants for topical compositions of the invention include, without limitation, polymers and co-polymers of ethylene glycol and propylene glycol, e.g., poloxamers, i.e., nonionic triblock copolymers composed of a central hydrophobic chain of polyoxypropylene (poly (propylene oxide)) flanked by two hydrophilic chains of polyoxyethylene (poly(ethylene oxide)). The approximate lengths of the two PEG blocks is, in some embodiments, an average of about 50-150 repeat units, e.g., about 100 repeat units while the approximate length of the propylene glycol block is an average of about 25-75 repeat unties, e.g., about 50-60 repeat units. In one preferred embodiment, the poloxamer is poloxamer 407, also known by the BASF trade name Pluronic F127, e.g., in an amount of from 0.3% to 50% by weight; or from 20% to 40% by weight, or from 25% to 35% by weight, or about 30% by weight of the formulation.

The pharmaceutical compositions provided herein may be formulated in any dosage forms that are suitable for topical administration, preferably but not necessarily for local effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon bases, including such as lard, benzoinated lard, olive oil, cottonseed oil, and other oils, white petrolatum; emulsifiable or absorption bases, such as hydrophilic petrolatum, hydroxystearin sulfate, and anhydrous lanolin; water-removable bases, such as hydrophilic ointment; water-soluble ointment bases, including polyethylene glycols of varying molecular weight; emulsion bases, either water-in-oil (W/O) emulsions or oil-in-water (OAV) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinyl-alcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppositoriy is about 2 to 3 g.

The pharmaceutical compositions provided herein for topical administration may be formulated to be immediate release or modified release, including delayed-, sustained-, pulsed-, controlled-, targeted, and programmed release.

Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile- or pulsed-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, NJ); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride. In another embodiment, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients in the compositions.

The pharmaceutical compositions provided herein in a modified release dosage form may be prepared by methods known to those skilled in the art, including direct compression, dry or wet granulation followed by compression, melt-granulation followed by compression.

Controlled Release Devices Osmotic

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," include, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphate, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-tolunesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

The semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients as described herein to promote performance or processing of the formulation.

The osmotic controlled-release dosage forms can be prepared according to conventional methods and techniques known to those skilled in the art (see, Remington: The Science and Practice of Pharmacy, supra; Santus and Baker, J. Controlled Release 1995, 35, 1-21; Verma et al., Drug Development and Industrial Pharmacy 2000, 26, 695-708; Verma et al., J. Controlled Release 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), hydroxylethyl cellulose, and other pharmaceutically acceptable excipients.

Multiparticulate Controlled Release Devices

The pharmaceutical compositions provided herein in a modified release dosage form may be fabricated as a multiparticulate controlled release device, which comprises a multiplicity of particles, granules, or pellets, ranging from about 10 µm to about 3 mm, about 50 µm to about 2.5 mm, or from about 100 µm to 1 mm in diameter. Such multiparticulates may be made by the processes know to those skilled in the art, including wet- and dry-granulation, extrusion/spheronization, roller-compaction, melt-congealing, and by spray-coating seed cores. See, for example, Multiparticulate Oral Drug Delivery; Marcel Dekker: 1994; and Pharmaceutical Pelletization Technology; Marcel Dekker: 1989.

Other excipients as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

In some topical embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). In some embodiments, a controlled release device, or a topical composition as described below which contains matrix material which effects a controlled or extended release of the active ingredients is introduced into a subject in proximity of the site of a pelvic floor muscle trigger point and/or specific areas of myofascial restriction detected upon palpation in a patient.

The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject. Other controlled release systems are discussed in the review by Langer (*Science* 249:1527-1533 (1990)), incorporated herein by reference.

Dosages

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration, preferably topically, orally or via injection. In addition, the compounds may be formulated as the sole active ingredient in the composition or may be combined with other active ingredients.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated there from for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In some embodiments, a therapeutically effective dosage should be from about 0.0001 mg to about 90 mg of each active ingredient (i.e., one or more of calcium channel blocker, L-arginine and/or corticosteroid) per kilogram of body weight per day, delivered topically, orally or by local injection as descried herein. In some embodiments, the calcium channel blocker is administered at a dosage of up to 120 mg/day, for example 90 mg/day, 85 mg/day, 80 mg/day, 75 mg/day, 70 mg/day, 65 mg/day, 60 mg/day, 55 mg/day, 50 mg/day, 45 mg/day, 40 mg/day, 35 mg/day, 30 mg/day, 25 mg/day, 20 mg/day, 15 mg/day, 10 mg/day, 5 mg/day, 2 mg/day or 1 mg/day.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 1%-3%, in another embodiment 2% and in still another embodiment, 1% to 3%. Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Oral Dosage

The oral dosage forms of the invention that contain calcium channel blockers, for example and not limitation nifedipine or diltiazem, will typically contain a lower dose of calcium channel blockers than is typically administered for use in indications such as hypertension. Thus, dosages for calcium channel blockers used in accordance with the methods and compositions of the present invention are typically less than about 95% of the dosages used for other presently approved indications.

For example, nifedipine dosages in accordance with the pharmaceutical compositions and methods of the invention can be from are typically up to about 120 mg/day, for example from 10 mg/day to about 90 mg/day, for example from 20 mg/day to about 90 mg/day, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 95, 100, 110, 115 or 120 mg/day; or for example 5, 15, 25, 35, 40, 45, 50, 55, 65, 70, 75, 80, 85, 90, 95, 100, 110, 115 or 120 mg/day; for example 5, 10, 15, 20, 25, 30, 35, 40, 45, 50, 55, 60, 65, 70, 75, 80, 85 or 90 mg/day.

In some preferred embodiments, the daily dose is administered once per day in an extended release composition.

In other embodiments, the daily dose is administered in smaller increments given multiple times per day, for example twice or three times per day, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 mg, taken 3 times daily; or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 mg, taken 2 times daily; or any combination of the above.

Similarly, diltiazem dosages in accordance with the pharmaceutical compositions and methods of the invention are typically less than 180 mg/day, for example 170 mg/day, 160 mg/day, 150 mg/day, 140 mg/day, 130 mg/day, 120 mg/day, 110 mg/day, 100 mg/day, 90 mg/day, 80 mg/day, 70 mg/day, 60 mg/day, 50 mg/day, 40 mg/day, 30 mg/day, 20 mg/day, 10 mg/day or 5 mg/day, taken for example and not limitation at smaller dosages several times per day, for example 2 or 3 times per day, in amounts that combined equal the daily values above. For extended-release dosage forms, diltiazem dosages in accordance with the pharmaceutical compositions and methods of the invention are typically less than 180 mg, taken once daily, for example and not limitation 1-170 mg, taken once daily; for example 170 mg, 160 mg, 150 mg, 140 mg, 130 mg, 120 mg, 110 mg, 100 mg, 90 mg, 80 mg, 70 mg, 60 mg, 50 mg, 40 mg, 30 mg, 20 mg, 10 mg or 5 mg, each taken once daily.

Topical Dosages

In some embodiments, the topical formulations of the present invention employ concentrations of calcium channel blocker and/or L-arginine that are therapeutically effective to treat the pelvic pain conditions described herein. Generally, the concentration of calcium channel blocker and/or L-arginine required for treatment by topical application to pelvic pain trigger points in accordance with the present invention are higher than for topical treatment of other conditions, for example open wounds such as anal fissures.

For example, in some embodiments, preferred concentrations and dosages of calcium channel blockers and/or L-arginine include a) for a topical formulation containing 0.5% active: 3 mg/dose, 6 mg for two doses, and 9 mg for 3 doses; b) for a topical formulation containing 1% active: 6 mg/dose, 12 mg for two doses, and 18 mg for 3 doses; c) for a topical formulation containing 2% active: 12 mg/dose, 24 mg for two doses, and 36 mg for 3 doses; and d) for a topical formulation containing 3% active: 18 mg/dose, 36 mg for two doses, and 54 mg for 3 doses.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

In accordance with another aspect of the disclosure herein, delivery of a topical pharmaceutical composition to a treatment site within the rectal cavity or the vaginal cavity of a human patient can be aided by an apparatus that includes an applicator member and a drug delivery device defined in part by a tubular member. The topical pharmaceutical composition is located in the tubular member. The tubular member is then placed partially into the rectal cavity or the vaginal cavity of the human patient. The drug delivery device can be used with an applicator member. The applicator member is adapted to apply the topical pharmaceutical composition to the treatment site. At least one of the drug delivery device or the applicator member can also be adapted to apply pressure to the treatment site, thereby allowing pressure based therapies such as trigger point release to be performed at the same time. As the applicator member is guided through the sleeve and thus into the rectal cavity or the vaginal cavity of the human patient, the topical pharmaceutical composition is moved out of the sleeve, and is directed to the treatment site by the applicator member. In implementations where the applicator member is a pressure applicator, pressure can be applied to the treatment site by the pressure applicator at the time of delivery of the topical pharmaceutical composition to the treatment site.

FIGS. 1A-1B show a delivery device 100 according to a first example and an applicator member 20.

The device 100 includes tubular member 110 having a hollow interior that extends from a first open end 112 to a second open end 114. A topical pharmaceutical composition 102 is disposed within the hollow interior of the tubular member 110.

In the illustrated example, the first open end 112 of the tubular member 110 is directed toward a treatment site 10, which can be a portion of the body of a human patient, such as an internal tissue of the rectal cavity or the vaginal cavity of the human patient. During use of the device 100, the tubular member is partially inserted into the rectal cavity or the vaginal cavity of the patient, such that the first open end 112 of the tubular member 110, is disposed within the patient's body, and the second open end 114 of the tubular member 110 is located outside of the patient's body.

The applicator member is adapted to be inserted through the hollow interior of the tubular member 110 of the device 100. The applicator member 20 can be an elongate member that has a tip 22 at one end thereof. The tip 22 is shaped and sized complementarily to the cross-sectional shape and size of the hollow interior of the tubular member 110. A maximum width or diameter can be approximately equal to or slightly smaller than an inside width or diameter of the hollow interior of the tubular member 110. In the illustrated example, the tip 22 is shaped as a partial sphere, and the remainder of the applicator member is substantially cylindrical. It should be understood, however, that other structural configurations can be utilized.

Initially, the tubular member 110 of the device 100 is inserted partially into the rectal cavity or the vaginal cavity of the human patient, via the patient's anal sphincter or vaginal opening. The first open end 112 of the tubular member 110 is located inside the rectal cavity or the vaginal cavity of the human patient, and is directed toward the treatment site 10. The tip 22 of the applicator member 20 is inserted into the hollow interior of the tubular member 110 through the second open end 114 of the tubular member 110 to define a first position (FIG. 1A) of the applicator member 20 with respect to the tubular member 110 of the device 100. The applicator member 20 is then moved through the hollow interior of the tubular member 110 toward the first open end 112 of the tubular member 110, until the tip 22 extends partially out of the first open end 112 of the tubular member 110 to define a second position (FIG. 1B). As the applicator member 20 moves through the tubular member 110, at least a portion of the topical pharmaceutical composition 102 is pushed out of the tubular member 110 by the applicator member 20, such that the topical pharmaceutical composition exits the tubular member via the first open end 112 thereof, and is directed to the treatment site 10 by the tip of the applicator member 20. Optionally, the tip 22 of the applicator member 20 can then be engaged with the treatment site 10 for applying pressure to the treatment site 10.

FIG. 2 shows a drug delivery device 200 according to a second example. The device 200 is similar to the device 100 except as noted. The device 200 includes a tubular member 210 having a hollow interior with a topical pharmaceutical composition 202 disposed therein. A first seal member 220 is disposed at a first end of the tubular member 210 and a second seal member 230 is disposed at a second end of the tubular member 210. The first and second seal members 220, 230 are removable members made of a material such as a film or a foil that is adhered to the tubular member 210 to seal the hollow interior of the device 200 prior to use. The first and second seal members are removed prior to use, and use of the device 200 is otherwise as described with respect to the device 100.

FIG. 3 shows a drug delivery device 300 according to a second example. The device 300 is similar to the device 100 except as noted. The device 300 includes a tubular member 310 having a hollow interior with a topical pharmaceutical composition 302 disposed therein. A first frangible member 320 is disposed within the hollow interior of the tubular member 310 and a second frangible member 330 is disposed within the hollow interior of the tubular member 310. The first and second frangible members 320, 330 are initially located such that the topical pharmaceutical composition 302 is disposed between them to seal and protect the topical pharmaceutical composition 302, and, are punctured during movement of an applicator member through the tubular member 310, thus releasing the topical pharmaceutical composition 302. Use of the device 300 is otherwise as described with respect to the device 100.

FIG. 4 shows a drug delivery device 400 according to a second example. The device 400 is similar to the device 100 except as noted. The device 400 includes a tubular member 410 having a hollow interior with a topical pharmaceutical composition 402 disposed therein. A first encapsulating material layer 420 is disposed within the hollow interior of the tubular member 410 and a second encapsulating material layer 430 is disposed within the hollow interior of the tubular member 410. The first and second encapsulating material layers 420, 430 can be a non-toxic biocompatible material that can be absorbed or passed by the patient's body, but are able to seal and protect the topical pharmaceutical composition 402 within the tubular member 410 at dry, room temperature conditions. As one example, the encapsulating material can be wax. As another example, the encapsulating material can be petroleum jelly. The first and second encapsulating material layers 420, 430 are initially located such that the topical pharmaceutical composition 402 is disposed between them to seal and protect the topical pharmaceutical composition 402, and, are pushed out of the tubular member 410 during movement of an applicator member through the tubular member 410, thus releasing the topical pharmaceutical composition 402. Use of the device 400 is otherwise as described with respect to the device 100.

Figure 5B:
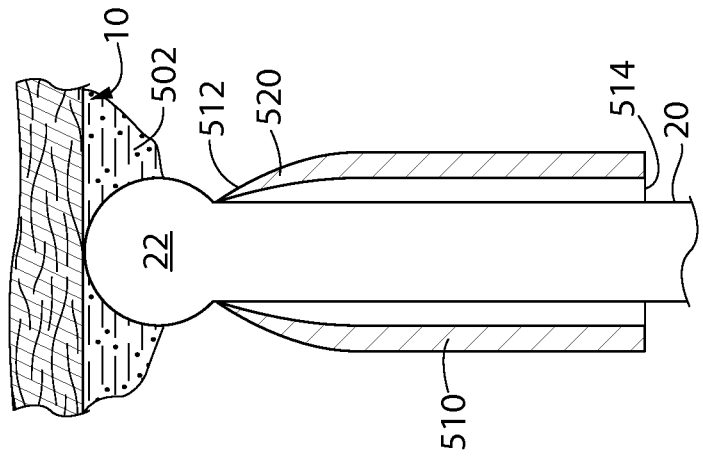
FIG. 5B is an illustration showing the fifth example drug delivery device and the pressure applicator in a second position.

FIGS. 5A-5B show a drug delivery device 500 according to a fifth example. The device 500 is similar to the device 100 except as noted, and includes a tubular member 510 having a topical pharmaceutical composition 502 disposed within a hollow interior thereof. The tubular member 510 extends from a first end 512, which is disposed within the patient's body and directed toward the treatment site 10 when in use, and a second end 514, which is an open end of the tubular member 510 that is disposed outside of the patient's body when in use. The first end 512 of the tubular member 510 has an approximately semi-spherical configuration that is defined by a plurality of segments 520. The plurality of segments 520 are each approximately wedge shaped portions of the semi-spherical configuration that are arrayed radially. Radially adjacent segments from the plurality of segments 520 are separated from one another by longitudinally extending slits. All of the segments meet one another at a location along the longitudinal axis of the tubular member 510 at the first end 512.

In a first position (FIG. 5A), the tip 22 of the applicator member 20 is disposed within the hollow interior of the tubular member 510 of the device 500, at a location that is adjacent to the second end 514 of the tubular member 510. As the tip 22 is moved through the tubular member 510 toward the first end 512, the tip 22 contacts the topical pharmaceutical composition 602 and displaces it within the tubular member 510, such that the topical pharmaceutical composition 502 is pushed through the tubular member 510 in response to movement of the tip 22 of the applicator member 20. When the tip 22 reaches the plurality of segments 520 at the first end 512 of the tubular member 510, each segment from the plurality of segments 520 moves radially outward, such as by flexing or deforming, in response to the pressure applied by engagement of the tip 22 and/or the topical pharmaceutical composition 502 with respect to the plurality of segments 520. This causes the plurality of segments 520 to move from a closed position in which they define the substantially semi-spherical configuration, to an open position (FIG. 5B), wherein an opening of a size sufficient to allow passage of the tip 22 of the applicator member 20 is defined between the plurality of segments 520 along the longitudinal axis of the tubular member 510. This allows the tip 22 to pass out of the device 500 at the first end thereof while directing the topical pharmaceutical composition 502 out of the device 500 to the treatment site 10. Optionally, the tip 22 of the applicator member 20 can then be engaged with the treatment site 10 for applying pressure to the treatment site 10.

FIGS. 6A-6B show a drug delivery device 600 according to a sixth example. The device 600 is similar to the device 100 except as noted, and includes a tubular member 610 having a topical pharmaceutical composition 602 disposed within a hollow interior thereof. The tubular member 610 extends from a first end 612, which is disposed within the patient's body and directed toward the treatment site 10 when in use, and a second end 614, which is an open end of the tubular member 610 that is disposed outside of the patient's body when in use. The first end 612 of the tubular member 612 has an approximately semi-spherical shape. One or more apertures extend through the wall of the tubular member 610 at the first end 612.

In a first position (FIG. 6A), the tip 22 of the applicator member 20 is disposed within the hollow interior of the tubular member 610 of the device 600, at a location that is adjacent to the second end 614 of the tubular member 610. As the tip 22 is moved through the tubular member 610 toward the first end 612, the tip 22 contacts the topical pharmaceutical composition 602 and displaces it within the tubular member 610, such that the topical preparation is pushed through the tubular member 610 in response to movement of the tip 22 of the applicator member 20. When the tip 22 reaches the first end 612 of the tubular member 610, the topical pharmaceutical composition 602 is forced through the apertures 620 to the exterior of the device 600 and toward the treatment site 10 (FIG. 6B). Optionally, the first end 612 of the device 600 can then be engaged with the treatment site 10 for applying pressure to the treatment site 10, in response to forces applied to the device 600 by the tip 22 of the applicator member 20.

FIGS. 7A-7B show a drug delivery device 700 according to a seventh example. The device 700 is similar to the device 100 except as noted, and includes a tubular member 710 having a topical pharmaceutical composition 702 disposed within a hollow interior thereof. The tubular member 710 extends from a first end 712, which is an open end of the tubular member 710 that is disposed within the patient's body and directed toward the treatment site 10 when in use, to a second end 714, which is an open end of the tubular member 710 that is disposed outside of the patient's body when in use. A stop surface is provided on the device 700 at the second end 714 and is configured to restrain further insertion of the device 700 with respect to the patient. The stop can be, for example, a flange 720 that is a substantially planar annular body that extends radially outward from the tubular member 710 at the second end 714 of the device 700.

In use, the device 700 is inserted into the patient's body until the flange 720 or other stop surface engages an external part 32 of the patient's body, thus restraining the device 700 against being inserted deeper into the patient's body. The external part 32 of the patient's body can be, for example, a portion of the patient's body that is located outside of and adjacent to an anal sphincter or vaginal opening of the patient. In a first position (FIG. 7A), the tip 22 of the applicator member 20 is disposed within the hollow interior of the tubular member 710 of the device 700, at a location that is adjacent to the second end 714 of the tubular member 710. As the tip 22 is moved through the tubular member 710 toward the first end 712, the tip 22 contacts the topical pharmaceutical composition 702 and displaces it within the tubular member 710 such that the topical pharmaceutical composition 702 is pushed through the tubular member 710 in response to movement of the tip 22 of the applicator member 20. When the tip 22 reaches the first end 712 of the tubular member 710, the topical pharmaceutical composition 702 exits the first end 712 of the device 700 along with the tip 22 of the applicator member 20, and the topical pharmaceutical composition 702 is delivered to the treatment site 10 by the tip 22 (FIG. 7B). Optionally, the tip 22 of the applicator member 20 can then be engaged with the treatment site 10 for applying pressure to the treatment site 10.

It should be understood that the features of the devices described with respect to FIGS. 1-7B can be combined in any desired fashion. As an example, the stop surface described with respect to the device 700 can be incorporated in the device 500. Other combinations of features are possible.

It should be understood that the devices shown in FIGS. 1-7B can be reusable devices or can be disposable devices.

The devices described with respect to FIGS. 1-7B can be utilized in a method for treating pelvic pain syndromes. The method includes placing a desired amount of the topical pharmaceutical composition within the device, inserting the device partially into a rectal or vaginal cavity of a patient, moving a part of an applicator member, such as a tip of the applicator member, into a hollow interior of the device, and moving the applicator member through the device such that the topical preparation is forced out of the device and is directed toward the treatment site. The method can further include applying pressure to the treatment site using at least one of the device or the applicator member. By this method, the applicator member can press the pharmaceutical composition against tender trigger points and areas of myofascial restriction that are higher inside the pelvic floor than would be accessible by application with a gloved finger, and the tip of the pressure applicator member can be guided by the patient's subjective senses, based on the sensations experienced by the patient.

Further devices include internal trigger point wands (see, e.g. U.S. Pat. Nos. 8,337,435 and 8,224,464, each of which is incorporated herein by reference in its entirety for all purposes).

Drug Applicator Sleeve

In accordance with another aspect of the disclosure herein, delivery of a topical pharmaceutical composition to a treatment site within the rectal cavity or the vaginal cavity of a human patient can be aided by the use of a drug applicator sleeve, which encases a medical probe, for example but not limitation an internal trigger point wand. In one embodiment, the drug applicator sleeve is an elongated tube with one open and one closed end. The probe or wand is inserted within the sleeve so that the probe is covered by the sleeve while in use inside the body. In this way, the sleeve is similar to an ultrasound probe cover or condom. Disposed along the length of the sleeve is a conduit capable of carrying and applying a topical pharmaceutical composition, as defined supra.

FIG. 8A shows an example of a representative drug applicator sleeve of the invention. Sleeve 500 has open end 501 and closed end 502. Integrally attached to sleeve 500 is conduit 600, having proximate open end 601 and distal open end 602. Proximate open end 601 has optionally attached thereto receiver 603, which is a receiving mechanism for a syringe, bulb or other reservoir commonly used to dispense medicaments, for example and not limitation a Luer-Lock for a syringe. Although FIG. 8A shows the conduit disposed on the outside of the sleeve, the invention also includes embodiments wherein the conduit is disposed inside the sleeve, and wherein the conduit forms part of the sleeve, as shown in cross sections 8b, 8c and 8d.

Conduit open end 602 can be adapted to open in a single location or multiple locations. In some embodiments, Conduit open end 602 is adapted to deliver a topical pharmaceutical composition to a specific place, for example by having a reduction in size at the opening so as to restrict the flow out of the conduit, and/or by having a different material at the end of open end 602.

Preferably, the drug applicator sleeve is configured to deliver topical pharmaceutical compositions, like those described supra, to points within the rectal or vaginal cavity. In some embodiments, the sleeve is used with a medical probe, for example but not limitation an internal trigger point wand (for example those described in U.S. Pat. Nos. 8,337,435 and 8,224,464). During use, a medical probe or trigger point wand is inserted into sleeve 500, and the probe or wand is used in its usual fashion to apply pressure to internal trigger points of, for example, the vaginal or rectal cavities. When application of a topical pharmaceutical composition is desired, a bulb, syringe or other suitable reservoir containing the composition is attached to receiver 603, and the bulb, syringe or other reservoir is employed to expel the composition through conduit 600 and out of conduit end 602 in precisely the desired location.

In some embodiments, the drug applicator sleeve is disposable. In some other embodiments, the drug applicator sleeve is reusable.

The drug applicator sleeve is preferably made of a flexible, biocompatible material which is preferably resistant to tears or punctures. The sleeve may be composed of any suitable elastomeric material; examples of suitable materials include but are not limited to: natural rubber latex, acrylonitrile, polyvinyl chloride, polyethylene, polypropylene, etc. Preferably, the sleeve is flexible, for example and not limitation having comparable flexibility to condoms, elastomeric medical examination gloves, and the like.

The conduit is preferably a flexible channel which is integral to, and resides passively on or in, the sleeve. The conduit can be made from any suitable elastomeric material, including those suitable for use as the sleeve. In some preferred embodiments, the conduit is made from the same or similar material as the sleeve. Thus, in some embodiments, the flexibility of both the conduit and the sleeve are comparable. In some embodiments, the conduit is disposed along the interior or exterior surface of the sleeve, or within the walls of the sleeve, as shown in FIGS. 8a-8c.

Typically, the drug applicator sleeve is from about 2 to about 10 inches long, and about one eighth (⅛) inch to about 2 inches in diameter, depending upon the probe or wand desired. The conduit can be from about one sixth (⅙) inch to about 1 inch in diameter, depending upon the properties of the desired pharmaceutical composition, e.g., flow properties, viscosity, etc. In some embodiments, the drug applicator sleeve is a smooth tube. In other embodiments, the drug applicator sleeve is adapted to conform to the surfaces of a probe or trigger point wand.

In some embodiments, the conduit is pre-filled with a pharmaceutical composition, such as for example a topical pharmaceutical composition of the invention as described herein. In some such embodiments, the pre-filled conduit enables users to administer pre-dosed amounts of compositions.

In some such embodiments, when pressure is applied to the conduit from the bulb, syringe or other reservoir, the composition is forced through the conduit and exits at end 602. In some embodiments, the conduit is unfilled, and is filled during use by expulsion of a topical pharmaceutical composition from, for example, a syringe, and into the conduit as described above.

Figure 9:
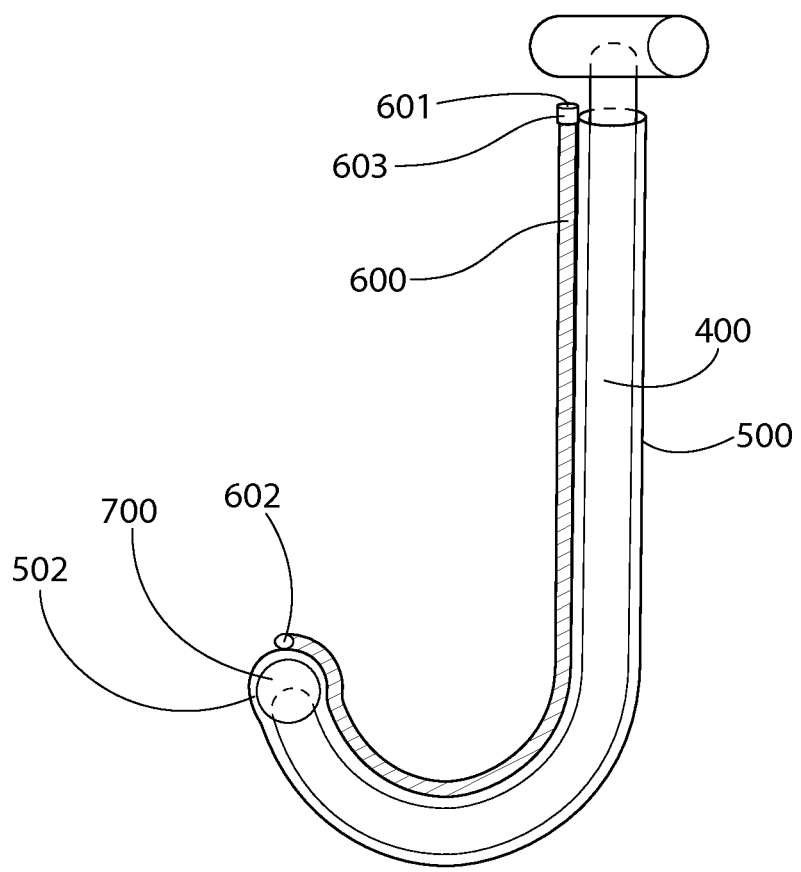
FIG. 9 shows an internal trigger point wand 400 inserted into a drug applicator sleeve of the invention.

FIG. 9 shows an internal trigger point wand 400 inserted into a drug applicator sleeve of the invention 500. Conduit 600 can be prefilled with a therapeutic composition or unfilled. Receiver 603 can be attached to a syringe, bulb or other reservoir as described above, and the contents of the reservoir and/or conduit deposited through open end 602 to the place of pressure application. When the patient has the wand inside the body and locates a trigger point, he or she would inject a small amount of the composition, for example a topical nifedipine composition as described herein, at the end of the wand. Then through the pressure of the trigger point release, the composition would be 'pressed' onto and "into" the tissue, abetting its local absorption. The patient would hold the pressure for 30-90 seconds as is customary for trigger point release and then move on to the next trigger point or tender area and repeat the procedure there.

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with pain conditions.

Provided herein is method (Method 1) for treating prostatitis category IIIA and/or IIIB in a male patient comprising administering to the male patient in need thereof a therapeutically effective amount of an active agent as described herein (i.e., a calcium channel blocker, or L-arginine, or a combination of a calcium channel blocker and L-arginine, or pharmaceutically acceptable salts, hydrates, solvates and prodrugs thereof). In some embodiments, the prostatitis category IIIA and/or IIIB is associated with pelvic floor muscle trigger points and/or areas of myofascial restriction.

Further provided herein is method (Method 2) for treating a condition selected from chronic pelvic pain, chronic pelvic pain without fissures or fistulas, chronically trigger pointed muscles, chronically trigger pointed pelvic floor muscles, chronic pelvic pain syndrome, pelvic floor myalgia, pelvic floor dysfunction, interstitial cystitis, levator ani syndrome, coccygodynia, prostatodynia, piriformis syndrome, vaginismus, anismus, anal sphincter pain, bowel movement pain, post bowel movement pain, ejaculatory pain or post ejaculatory pain in a patient comprising administering to the patient in need thereof a therapeutically effective amount of an active agent as described herein. In some embodiments, the condition is associated with pelvic floor muscle trigger points and/or areas of myofascial restriction. In some embodiments, the chronic pelvic pain exists without fissures or fistulas or evidence of other pathology in external or internal anal sphincters; and the chronic pelvic pain syndrome exists with pain referring trigger points. In some embodiments, the condition is associated with pelvic floor muscle trigger points and/or areas of myofascial restriction Further provided herein is method (Method 3) for treating sitting pain, post bowel movement pain, rectal pain, tailbone pain, urinary frequency, urinary urgency, urinary hesitancy, perineal pain, penile pain, sexual dysfunction and reduced level of ejaculate or reduced penile erection in a patient comprising administering to the patient in need thereof a therapeutically effective amount of an active agent as described herein. In some embodiments, the sitting pain, post bowel movement pain, rectal pain, tailbone pain, urinary frequency, urinary urgency, urinary hesitancy, perineal pain, penile pain, sexual dysfunction and reduced level of ejaculate or reduced penile erection exists in the presence of or is associated with pelvic floor muscle trigger points and/or areas of myofascial restriction.

Further provided herein is method (Method 4) for treating myofascial pain in muscle tissue of a patient who has one or more trigger points in the muscle tissue comprising administering to the one or more trigger points of the patient in need thereof a therapeutically effective amount of an active agent as described herein.

Further provided herein is method (Method 5) for reducing the pain/sensitivity of pelvic floor muscle trigger points and specific areas of myofascial restriction detected upon palpation in a patient, comprising applying to the patient in need thereof a therapeutically effective amount of an active agent as described herein. In some embodiments of Method 5, the patient is a female. In some such embodiments, the pelvic pain is not associated with hypertonus.

Further provided herein is method (Method 6) for treating pelvic pain or in a female patient comprising administering to the patient in need thereof a therapeutically effective amount of an active agent as described herein. In some embodiments of Method 6, the pelvis of the female or male patient is not hypertonic. In some embodiments of Method 6, the calcium channel blocker or 1-arginine is not administered to the vagina of the patient.

Further provided herein is method (Method 7) for reducing or resolving trigger point pain, sensitivity or activity in muscle of a patient in need thereof comprising contacting the muscle with a therapeutically effective amount of an active agent as described herein. In some embodiments, the therapeutically effective amount of the active agent is administered to, near to or adjacent to one or more external or internal trigger points of the muscle. In some embodiments, the muscle is located in the anal sphincter, beyond the internal anal sphincter in the pelvic floor, in the superior portions of the levator ani muscles, in the coccygeus muscles, in the obturator internus muscles, in the internal portions of the piriformis; in an external muscle; in the rectus abdominus, in a gluteal muscle, in an adductor muscle, or the quadratus lumborum. In some embodiments, the contacting comprises administering the active agent to the pelvic floor muscle of the patient; or to one or more specific trigger points in the pelvic floor muscle of the patient; or near to, or adjacent to, one or more specific trigger points in the pelvic floor muscle of the patient.

In further embodiments, the present inventions provides methods (Method 8) for the reduction and/or resolution of trigger point pain, sensitivity or activity in a muscle of a patient in need thereof, comprising administering a therapeutically effective amount of a calcium channel blocker, or L-arginine, or a combination of a calcium channel blocker and L-arginine, or pharmaceutically acceptable salts, hydrates, solvates and prodrugs thereof to the muscle of the patient. In some embodiments, the one or more trigger points are external trigger points. In some embodiments, the active agent is administered by injection, for example directly into or near to, or adjacent to the trigger point by the patient or another, for example a doctor or physical therapist. In some embodiments, the active agent is administered manually. In some embodiments, the active agent is administered directly to, near to, or adjacent to one or more trigger points of the muscle. In some embodiments, the method comprises self-treatment. In other embodiments, the method is comprises treatment by another. In other embodiments, the method comprises administration of the active agent by the patient as part of a self-treatment program, for example by using an internal trigger point wand.

In further embodiments, the present inventions provides methods (Method 9) for relieving muscle soreness or pain in a patient in need thereof, comprising applying to the muscle a topical composition comprising a calcium channel blocker, or a pharmaceutically acceptable salt, hydrate, solvate or prodrug thereof. In some such embodiments, a topical composition is applied to the muscle. In some embodiments, the topical composition is a balm, which can comprise one or more analgesics, fragrances and excipients, for example and not limitation menthol, menthone, camphor, pulegol, isopulegol, cineole, mint oil, peppermint oil, spearmint oil, eucalyptus oil, 3-(1-menthoxy)propane-1,2-diol, N-alkyl-p-menthane-3-carboxamide, 2-methyl-3-(1-menthoxy)propane-1,2-diol, p-menthane-3,8-diol, 2-(1-menthoxy)ethan-1-ol, 3-(1-menthoxy)propan-1-ol, 4-(1-menthoxy)butan-1-ol, menthyl 3-hydroxybutanoate, menthyl lactate, menthone glycerin ketal, N-methyl-2,2-isopropylmethyl-3-methylbutane amide, menthyl glyoxylate cajuput oil, clove oil, dementholized mint oil and paraffin petrolatum.

In further embodiments, the present inventions provides methods (Method 10) for relieving one or more symptoms of carpal tunnel syndrome in a patient in need thereof, comprising administering to a patient in need thereof a pharmaceutical composition comprising a calcium channel blocker, or a pharmaceutically acceptable salt, hydrate, solvate or prodrug thereof. In some such embodiments, a topical composition is applied to the muscle. In other such embodiments, an oral pharmaceutical composition is administered.

The present invention further provides a method (Method 11) of treating a condition selected from chronic pelvic pain, chronic pelvic pain without fissures or fistulas, chronically trigger pointed muscles, chronically trigger pointed pelvic floor muscles, chronic pelvic pain syndrome, pelvic floor myalgia, pelvic floor dysfunction, interstitial cystitis, levator ani syndrome, coccygodynia, prostatodynia, piriformis syndrome, vaginismus, anismus, anal sphincter pain, bowel movement pain, post bowel movement pain, ejaculatory pain or post ejaculatory pain; chronic pelvic pain without evidence of other pathology in external or internal anal sphincters; pelvic pain with pain referring trigger points; pelvic pain with associated with pelvic floor muscle trigger points and/or areas of myofascial restriction; sitting pain, post bowel movement pain, rectal pain, tailbone pain, urinary frequency, urinary urgency, urinary hesitancy, perineal pain, penile pain, vaginismus, anismus, sexual dysfunction and reduced level of ejaculate or reduced penile erection, urinary sphincter spasms, urethral sphincter spasms, post urinary pain, rectal sphincter spasms, proctalgia fugax and myofascial pain in muscle tissue of a patient who has one or more trigger points in the muscle tissue; the method comprising treating a patient in need thereof with a dilator, such as an anal, vaginal or urethral dilator (including pediatric dilators thereof).

In some embodiments of Method 11, dilators for use in accordance with the methods of the invention are preferably are preferably sized from ¼ inch in diameter to 1½" inches in diameter, for example in size increments of ¹⁄₁₆ or ⅛ of an inch. In some preferred embodiments, the methods of the invention comprise the use of the dilators daily, or more than once daily, for example twice daily, three times daily, or more, for a period of time at each instance, for example of from about 10 minute to about 40 minutes, or about 20 minutes to about 30 minutes. In some embodiments, the methods of the invention are employed for a fixed period of time, for example on a single day, for several days, a week, 1 month, or longer. In some embodiments, treatment with the methods of the invention is continued until symptoms are resolved. In some embodiments, treatment further comprises the progressive transitioning from smaller sized dilators to larger sized dilators.

The invention further provides a kit containing a plurality of dilators having sizes from about ¼ inch in diameter to about 1½" inches in diameter, in size increments of for example ¹⁄₁₆ or ⅛ of an inch. In preferred embodiments, the dilator kits include an application guide for instructing the patient or health care professional in the proper use of the dilator in accordance with the methods of the invention.

In some embodiments, Method 11 further comprises the administration of a calcium channel blocker, or a pharmaceutically acceptable salt thereof, or a pharmaceutical composition thereof, as described herein. The calcium channel blocker can be administered orally (e.g., as an oral composition), for example, in the form of a pill, tablet or capsule; or topically (e.g., as a topical composition), such as an ointment, gel or paste. In some embodiments, the calcium channel blocker, or pharmaceutical composition thereof, is administered prior to use of the dilator, for example from 5 minutes to 60 minutes prior to dilator use, from 10 minutes to 60 minutes prior to dilator use; from 20 minutes to 60 minutes prior to dilator use; or from 30 to 60 minutes prior to dilator use. In some embodiments, a local anesthetic agent may also be administered concomitantly or sequentially with dilator use. In some embodiments, the local anesthetic is a component of the pharmaceutical composition containing the calcium channel blocker. In some preferred embodiments, the calcium channel blocker used with Method 11 is nifedipine.

In some embodiments of the methods 1-11 described herein, the active agent includes a corticosteroid, for example cortisone or hydrocortisone.

In some embodiments of each of the methods described herein, the methods are performed in the presence of muscle hypertonicity. In some embodiments of each of the methods described herein, the methods are performed in the absence of muscle hypertonicity.

In some embodiments of each of the methods described herein, the methods include treating the recited pain condition wherein the condition is associated with specific areas of myofascial restriction, for example those detected upon palpation in a patient.

In some embodiments of each of the methods described herein, the administration of the active agent is performed manually, or using an applicator such as a syringe or an internal trigger point wand as described herein, or via injection. In some embodiments the administration of the active agent is performed via injection into, near to or adjacent to the muscle. In some embodiments, the active agent is injected directly into, near to or adjacent to one or more trigger points of the muscle. In some embodiments, the trigger points are external trigger points, and in other embodiments, the trigger points are internal trigger points.

In some embodiments of each of the methods and compositions described herein, the active agent is present in a pharmaceutical composition that further comprises one or more pharmaceutically acceptable carriers, and optionally an anesthetic.

Further provided herein are any of the foregoing methods wherein the calcium channel blocker is a dihyropyridine, a phenylalkylamine, a benzothiapene, zicotonide or a nonselective calcium channel blocker.

Further provided herein are any of the foregoing methods wherein the dihydropyridine channel blocker is amlopidine, aranidipine, azelnidipine, barnidipine, benidipine, cilnidipine, clevidipine, isradipine, efonidipine, felodipine, lacidipone, lercanidipine, manidipine, nicardipine, nifedipine, nilvadipine, nimodipine, nisoldipine, nitrendipine or pranidipine Further provided herein are any of the foregoing methods wherein the phenylalkylamine calcium channel blocker is varapamil, gallopamil or fendiline.

Further provided herein are any of the foregoing methods wherein the benzothiazepine calcium channel blocker is diltiazem.

Further provided herein are any of the foregoing methods wherein the non-selective calcium channel blocker is mibefradil, bepridil, flunarizine, fluspirilene or fendiline.

Further provided herein are any of the foregoing methods wherein the calcium channel blocker is diltiazem or nifedipine.

Further provided herein are any of the foregoing methods wherein the calcium channel blocker is nifedipine.

Further provided herein are any of the foregoing methods comprising administering to the patient in need thereof a pharmaceutical composition comprising the therapeutically effective amount of the calcium channel blocker, or L-arginine, or combination of a calcium channel blocker and L-arginine, or pharmaceutically acceptable salts, hydrates, solvates and prodrugs thereof. In some embodiments, the pharmaceutical composition further comprises a therapeutically effective amount of a local anesthetic. In some embodiments, the local anesthetic is lidocaine.

Further provided herein are any of the foregoing methods wherein the pharmaceutical composition further comprises a controlled release agent.

Further provided herein are any of the foregoing methods wherein the pharmaceutical composition comprises a poloxamer. In some such embodiments, the poloxamer is poloxamer 407®.

Further provided herein are any of the foregoing methods wherein the pharmaceutical composition comprises diltiazem or nifedipine.

Further provided herein are any of the foregoing methods wherein the pharmaceutical composition comprises nifedipine and a controlled release agent.

Further provided herein are any of the foregoing methods wherein the pharmaceutical composition comprises diltiazem and a controlled release agent.

Further provided herein are any of the foregoing methods wherein the pharmaceutical composition is topical.

Further provided herein are any of the foregoing methods wherein the topical pharmaceutical composition is applied to a treatment site.

Further provided herein are any of the foregoing methods wherein the treatment site is the inside of an anal opening or the pelvic floor muscles of the patient.

Further provided herein are any of the foregoing methods wherein the treatment site is the vaginal opening of a female patient.

Further provided herein are any of the foregoing methods wherein the topical pharmaceutical composition is applied to the anal sphincter or vaginal opening of the patient by inserting a pressure applicator device in a rectal cavity or a vaginal cavity of the human patient through the anal sphincter or vaginal opening; and applying pressure at an internal trigger point or area of myofascial restriction within the rectal cavity or the vaginal cavity with the pressure applicator device to apply the topical pharmaceutical composition.

Further provided herein are any of the foregoing methods wherein the topical pharmaceutical composition is applied manually, as a suppository or using an applicator. In some embodiments, the topical pharmaceutical composition is applied using a disposable or reusable rectal syringe, or a pressure applicator device.

Further provided herein are any of the methods described herein further comprising the step of identifying a patient in need of the treatment.

Further provided herein are any of the foregoing methods wherein the pharmaceutical composition comprises the calcium channel blocker in an amount of from 0.5% to 5%; or from 0.5% to 4%; or from 0.5% to 3%; or from 0.5% to 2%; or from 0.5% to 1.5%; or 1%, 2%, 3%, 4% or 5% by weight. In some such embodiments, the calcium channel blocker is diltiazem or nifedipine.

The present invention further provides topical pharmaceutical compositions comprising a calcium channel blocker, or L-arginine, or a combination of a calcium channel blocker and L-arginine, or pharmaceutically acceptable salts, hydrates, solvates and prodrugs thereof, in an amount therapeutically effective to treat one or more of chronic pelvic pain, trigger pointed pelvic floor muscles, chronic pelvic pain syndrome, pelvic floor myalgia, pelvic floor dysfunction, interstitial cystitis, levator ani syndrome, coccygodynia, prostatodynia, piriformis syndrome, anal sphincter pain, bowel movement pain, post bowel movement pain, ejaculatory pain, post ejaculatory pain, sitting pain, post bowel movement pain, rectal pain, tailbone pain, urinary frequency, urinary urgency, urinary hesitancy, perineal pain, penile pain, sexual dysfunction, reduced level of ejaculate or reduced penile erection, myofascial pain in muscle tissue of a patient who has one or more trigger points in the muscle tissue, conditions characterized by muscle spasm or soreness such as, for example, urinary sphincter spasms, urethral sphincter spasms, post urinary pain, rectal sphincter spasms and proctalgia fugax, and the pain/sensitivity of pelvic floor muscle trigger points and specific areas of myofascial restriction detected upon palpation in a patient. In some embodiments, the calcium channel blocker is diltiazem or nifedipine.

In some embodiments of each of the topical and injectable pharmaceutical compositions described herein, the composition can include a therapeutically effective amount of a corticosteroid, for example and not limitation cortisone and hydrocortisone (cortisol). In some embodiments, the corticosteroid is present in the pharmaceutical composition in an amount of from about from 0.01% to 5% by weight; 0.05% to 4% by weight; 0.1% to 4% by weight; 0.1% to 3% by weight; from 0.1% to 2% by weight; or from 0.5% to 1.5% by weight, or about 0.1%, 0.5%, 1%, 1.5%, 2%, 2.5%, 3%, 4% or 5% by weight.

In some embodiments, the topical pharmaceutical composition comprises a poloxamer, for example poloxamer 407®. While not wishing to be bound by any particular theory, it is believed that poloxamers, and in particular poloxamer 407® are advantageous in that the combination of the poloxamer plus calcium channel blocker, for example and not limitation nifedipine or diltiazem, and/or L-arginine, forms a unique composition that has bioadhesive and healing properties. It also is believed that the composition has the beneficial property of increasing in viscosity or solidity as its temperature increases. These properties may be beneficial in promoting the local administration of the active ingredient(s), and resisting systemic absorption. Indeed, in the methodology discussed in the Wise publications mentioned above, patients are taught the anatomy of pelvic floor, and the application of pressure in specific areas in the pelvic floor to relieve trigger point activity, either manually or using an applicator such as a syringe or an internal trigger point wand as described in, e.g. U.S. Pat. Nos. 8,337,435 and 8,224,464, each of which is incorporated herein by reference in its entirety for all purposes. In some embodiments of the present invention, the patient uses the wand to deliver a bioadhesive product of the invention; e.g., a composition comprising poloxamer 407® and a calcium channel blocker, L-arginine, or both, to the specific area. It is believed that the bioadhesive properties of the composition retards migration of the composition, thus promoting the retention of active ingredients in the specific place it is most effective, and thus also minimizing systemic absorption.

In some embodiments, the topical pharmaceutical composition comprises a local anesthetic, for example lidocaine.

In some embodiments, the topical pharmaceutical composition comprises diltiazem or nifedipine in an amount of from 0.5% to 5% by weight; 0.2% to 5% by weight; 0.5% to 4% by weight; 0.5% to 3% by weight; 0.5% to 2% by weight; or from 0.5% to 1.5% by weight; or about 0.5%, 1%, 1.5%, 2%, 2.5%, 3%, 4% or 5% by weight.

In some embodiments, the topical pharmaceutical composition comprises L-arginine in an amount of from 0.5% to 5% by weight; 0.4% to 4% by weight; 0.5% to 4% by weight; 0.5% to 3% by weight; 0.5% to 2% by weight; or from 0.5% to 1.5% by weight; or about 0.5%, 1%, 1.5%, 2%, 2.5%, 3%, 4% or 5% by weight.

In some preferred embodiments, for example those comprising nifedipine as a calcium channel blocker, preferred dosages include a) for a topical formulation containing 0.5% nifedipine: 3 mg/dose, 6 mg for two doses, and 9 mg for 3 doses; b) for a topical formulation containing 1% nifedipine: 6 mg/dose, 12 mg for two doses, and 18 mg for 3 doses; c) for a topical formulation containing 2% nifedipine: 12 mg/dose, 24 mg for two doses, and 36 mg for 3 doses; and d) for a topical formulation containing 3% nifedipine: 18 mg/dose, 36 mg for two doses, and 54 mg for 3 doses.

In some embodiments, the invention provides pharmaceutical compositions for oral administration in accordance with the methods described herein, comprising nifedipine in an amount of from 1, 2, 3, 4, 5, 6, 7, 8, 9, 11, 12, 13, 14, 15, 16, 17, 18, 19, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, 89, 100, 110 or 120 mg; or 11, 12, 13, 14, 15, 16, 17, 18, 19, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, or 89 mg; or 21, 22, 23, 24, 25, 26, 27, 28, 29, 31, 32, 34, 36, 38, 40, 42, 44, 46, 48, 50, 52, 54, 56, 58, 59, 62, 64, 66, 68, 70, 72, 74, 76, 78, 80, 82, 8, 86, 88, or 89 mg. In some embodiments, the pharmaceutical composition is an extended release composition. In some embodiment, the pharmaceutical composition is an immediate release composition.

In some embodiments the extended release composition contain nifedipine in an amount of 3 mg, 5 mg, 6 mg, 9 mg, 12 mg, 15 mg, 18 mg, 21 mg, 24 mg, 25 mg, 27 mg or 29 mg of nifedipine; or in an amount of 32 mg, 35 mg, 38 mg, 40 mg, 41 mg, 45 mg, 48 mg, 50 mg, 55 mg, 58 mg, 62 mg, 65 mg, 70 mg, 75 mg, 80 mg, 85 mg or 89 mg of nifedipine.

In some embodiments, the invention provides an extended release pharmaceutical composition for oral administration in accordance with the methods described herein, comprising diltiazem in an amount of from 20 mg to 170 mg, for example for example 2, 5, 10, 20, 30, 40, 50, 60, 70, 80, 90, 100, 110, 120, 130, 140, 150, 160 or 170 mg of diltiazem.

In some further embodiments, the invention provides an immediate release pharmaceutical composition for oral administration comprising nifedipine in an amount of from 1-27 mg, for example 1 mg, 2 mg, 3 mg, 6 mg, 9 mg, 12 mg, 15 mg, 18 mg, 21 mg, 24 mg or 27 mg of diltiazem.

In some embodiments, the invention provides an extended release, enterically coated dosage form comprising an active ingredient that is a calcium channel blocker, for example nifedipine or diltiazem, wherein the dosage form additionally comprises one or more mucoadhesive polymers, and, optionally, one or more delayed release polymers. The invention further provides a method for simultaneously delivering a systemic and local acting dose of a calcium channel blocker, comprising administering such a dosage form.

In some embodiments, the invention provides the foregoing methods described herein, the methods comprising the administration of a pharmaceutical composition for oral administration as described herein.

Further provided in accordance with the present invention is a method for treating chronic pelvic pain, chronically trigger pointed pelvic floor muscles, chronic pelvic pain syndrome, pelvic floor myalgia, pelvic floor dysfunction, interstitial cystitis, levator ani syndrome, coccygodynia, prostatodynia, piriformis syndrome, anal sphincter pain, bowel movement pain, post bowel movement pain, ejaculatory pain, post ejaculatory pain, sitting pain, post bowel movement pain, rectal pain, tailbone pain, urinary frequency, urinary urgency, urinary hesitancy, perineal pain, penile pain, vaginismus, anismus, sexual dysfunction, reduced level of ejaculate or reduced penile erection, myofascial pain in muscle tissue of a patient who has one or more trigger points in the muscle tissue, or the pain/sensitivity of pelvic floor muscle trigger points detected upon palpation in a patient; the method comprising:

a) palpating a patient to detect said trigger points; and
b) administering to the identified trigger points and/or specific areas of myofascial restriction of the patient a therapeutically effective amount of a calcium channel blocker, or L-arginine, or a combination of a calcium channel blocker and L-arginine, or pharmaceutically acceptable salts, hydrates, solvates and prodrugs thereof, as described in the foregoing methods and compositions herein. The administration in some embodiments can be performed by the patient, a therapist, or another.

The present invention also provides compositions and methods for treatment of anal fissures, and alleviation of symptoms of anal fissures, which in one embodiment comprises perianal or intrarectal administration of a topical composition comprising the active ingredients according to the present invention, for example nifedipine or diltiazem, and in a further embodiment comprises oral administration of the active ingredients according to the present invention, for example nifedipine or diltiazem, each to a patient in need thereof. In some embodiments, the methods comprise administration of a topical pharmaceutical composition comprising nifedipine in an amount of from 0.3-2%; or an oral dose of from 11 mg to 90 mg of nifedipine, as described above; or a topical pharmaceutical composition comprising diltiazem in an amount of from 1-3%; or an oral dose of from 120 mg to 360 mg of diltiazem; each optionally containing one or more excipients, for example and not limitation a poloxamer, for example poloxamer 407.

The present invention further provides methods for treating a condition characterized by muscle spasm or soreness, comprising administering to a patient in need thereof a therapeutically effective amount of a calcium channel blocker, or L-arginine, or a combination of a calcium channel blocker and L-arginine, or pharmaceutically acceptable salts thereof. In some embodiments, the condition is selected from urinary sphincter spasms, urethral sphincter spasms, post urinary pain, rectal sphincter spasms and proctalgia fugax In some such embodiments, the methods comprise oral or topical administration of the calcium channel blocker, or pharmaceutically acceptable salt thereof, preferably in an extended release oral dosage form. In some embodiments of the foregoing, the calcium channel blocker is selected from nifedipine and diltiazem.

The present invention further provides an apparatus for applying a topical pharmaceutical composition to a treatment site that is located within a rectal cavity or a vaginal cavity of a human patient, the apparatus comprising: a tubular member, wherein the topical pharmaceutical composition is located inside the tubular member prior to application of the topical preparation to the treatment site; and an applicator member that is receivable in the sleeve wherein, the applicator member is movable within the tubular member from a first position to a second position to cause at least a portion of the topical preparation to be moved out of the sleeve and thereby applied to the treatment site.

In some embodiments of the apparatus, wherein the tubular member is adapted to extend into an opening of the rectal cavity or the vaginal cavity of the human patient. In some further embodiments of the apparatus, the tubular member extends from a first end to a second end, wherein the first end is disposed within the rectal cavity or the vaginal cavity of the human patient during application of the topical pharmaceutical composition to the treatment site and the second end is disposed outside of the rectal cavity or the vaginal cavity of the human patient during application of the topical pharmaceutical composition to the treatment site.

In some further embodiments of the apparatus, the tubular member extends from a first end to a second end, wherein the first end is disposed within the rectal cavity or the vaginal cavity of the human patient during application of the topical pharmaceutical composition to the treatment site and the second end is disposed outside of the rectal cavity or the vaginal cavity of the human patient during application of the topical pharmaceutical composition to the treatment site. In some such embodiments, the first end has a semi-spherical configuration defined by a plurality of segments that are movable in response to movement of the applicator member from the first position to the second position.

In some embodiments, the apparatus further comprises a stop surface that extends outward from the tubular member for restraining further insertion of the tubular member with respect to the rectal cavity or the vaginal cavity of the human patient.

In some embodiments, the pharmaceutical compositions described herein are applied manually (for example by using a gloved finger), or using an applicator as described herein, for example and not limitation the pressure applicator device described above, or using commercially available disposable or re-useable rectal syringes. Accordingly, the present invention further provides kits comprising one or more disposable rectal syringes and a pharmaceutical composition according to the invention. The invention further provides kits comprising one or more re-useable or disposable rectal syringes and a pharmaceutical composition according the invention. The invention further provides kits comprising one or more applicators as described herein and a pharmaceutical composition according the invention.

In some embodiments of each of the foregoing kits, the syringes or applicators can be pre-filled with the pharmaceutical composition.

In some embodiments, the pharmaceutical compositions described herein are applied using an internal trigger point wand. Such wands are described in, e.g. U.S. Pat. Nos. 8,337,435 and 8,224,464, each of which is incorporated herein by reference in its entirety for all purposes.

In some embodiments, the invention provides drug applicator sleeves comprising: a tubular member having an open end and a closed end; and an integral conduit disposed thereon or therein; wherein: the tubular member has a length of from about 2 to about 10 inches long, and a diameter of from about ⅛ inch to about 2 inches; the integral conduit has a diameter of from ⅙ inch to about 1 inch, and also optionally comprises a receiver for interfacing with a syringe, bulb or other reservoir. In some embodiments, the integral conduit is disposed on or in the tubular member substantially along its length.

In some embodiments, the drug applicator sleeve is a smooth tube, and in other embodiments, drug applicator sleeve is adapted to conform to the surfaces of a probe or trigger point wand. In some embodiments, the integral conduit comprises a receiver for interfacing with a syringe, bulb or other reservoir.

In some of each of the foregoing embodiments, the conduit is pre-filled with a topical pharmaceutical composition. In some such embodiments, the topical pharmaceutical composition is a composition of the invention as described herein.

Also provided in accordance with the invention are assemblies comprising a medical probe or trigger point wand and a drug applicator sleeve as described herein.

Also provided in accordance with the present invention are:
a) the use of diltiazem, nifedipine or L-arginine to treat prostatitis category IIIA and/or IIIB in a male patient;
b) the use of diltiazem, nifedipine or L-arginine to treat chronic pelvic pain, chronic pelvic pain syndrome, pelvic floor myalgia, pelvic floor dysfunction, interstitial cystitis, levator ani syndrome, coccygodynia, prostatodynia, piriformis syndrome, anal sphincter pain, bowel movement pain, post bowel movement pain, ejaculatory pain or post ejaculatory pain;
c) the use of diltiazem, nifedipine or L-arginine to treat sitting pain, post bowel movement pain, rectal pain, tailbone pain, urinary frequency, urinary urgency, urinary hesitancy, perineal pain, penile pain, sexual dysfunction and reduced level of ejaculate or reduced penile erection;
d) the use of diltiazem, nifedipine or L-arginine to treat myofascial pain in muscle tissue of a patient who has one or more trigger points in the muscle tissue;
e) the use of diltiazem, nifedipine or L-arginine to reduce the pain/sensitivity of pelvic floor muscle trigger points detected upon palpation in a patient used topically and applied to the patient manually, such as with a gloved finger; and
f) the use of diltiazem, nifedipine or L-arginine to treat pelvic pain in a female patient;
g) the use of diltiazem, nifedipine or L-arginine to treat anal sphincter pain, bowel movement pain, post bowel movement pain, ejaculatory pain, ejaculatory discomfort, post ejaculatory pain, sitting pain, rectal pain, tailbone pain, urinary frequency, urinary urgency, urinary hesitancy, perineal pain, penile pain, sexual dysfunction, reduced level of ejaculate or reduced penile erection, nonbacterial prostatitis, slow urinary flow, reduced urinary flow, post ejaculatory discomfort, urinary or urethral sphincter spasms and post urinary pain, rectal sphincter spasms, proctalgia fugax, chronic pelvic pain, pelvic floor muscles containing trigger points and areas of myofascial restriction, chronic pelvic pain syndrome, pelvic floor myalgia, pelvic floor dysfunction, interstitial cystitis, levator ani syndrome, coccygodynia, prostatodynia, prostadynia, piriformis syndrome, anal sphincter pain, bowel movement pain, ejaculatory pain, ejaculatory discomfort, post bowel movement pain, anal fissures or tear in the anorectal/anal sphincter area, myofascial pain in muscle tissue of a patient who has one or more trigger points in the muscle tissue, and the pain/sensitivity of pelvic floor muscle trigger points and specific areas of myofascial restriction detected upon palpation in a patient.

The invention provides, in one embodiment, a method (Method 1) for treating prostatitis category IIIA and/or IIIB in a male patient comprising administering to the male patient in need thereof a therapeutically effective amount of a calcium channel blocker, or L-arginine, or a combination of a calcium channel blocker and L-arginine, or pharmaceutically acceptable salts, for example:
1.1. Method 1, wherein the calcium channel blocker is nifedipine or diltiazem;
1.2. Method 1 or 1.1, wherein the prostatitis category IIIA and/or IIIB is associated with pelvic floor muscle trigger points.
1.3. Any Method 1-1.2, wherein the administering, applying or contacting comprises administering the calcium channel blocker, or L-arginine, or combination of a calcium channel blocker and L-arginine, or pharmaceutically acceptable salts thereof, to the pelvic floor muscle of the patient.
1.4. Method 1.3, wherein the administering, applying or contacting comprises administering the calcium channel blocker, or L-arginine, or combination of a calcium channel blocker and L-arginine, or pharmaceutically acceptable salts thereof, to one or more specific trigger points in the pelvic floor muscle of the patient.

In further embodiments, the invention provides a method (Method 2) for treating a condition selected from chronic pelvic pain, chronic pelvic pain without fissures or fistulas, chronically trigger pointed pelvic floor muscles, chronic pelvic pain syndrome, pelvic floor myalgia, pelvic floor dysfunction, interstitial cystitis, overactive bladder, levator ani syndrome, coccygodynia, prostatodynia, piriformis syndrome, anal sphincter pain, bowel movement pain, post bowel movement pain, vaginismus, anismus, ejaculatory pain or post ejaculatory pain in a patient comprising administering to the patient in need thereof a therapeutically effective amount of a calcium channel blocker, or L-arginine, or a combination of a calcium channel blocker and L-arginine, or pharmaceutically acceptable salts thereof, for example:
2.1. Method 2, wherein the calcium channel blocker is nifedipine or diltiazem;
2.2. Method 2 or 2.1, wherein the chronic pelvic pain exists with or without fissures or fistulas or evidence of hypertonus or other pathology in external or internal anal sphincters; and the chronic pelvic pain syndrome exists with pain containing or referring trigger points.
2.3. Method 2.2, wherein the condition is associated with pelvic floor muscle trigger points.
2.4. Any Method 2-2.2, wherein the administering, applying or contacting comprises administering the calcium channel blocker, or L-arginine, or combination of a calcium channel blocker and L-arginine, or pharmaceutically acceptable salts thereof, to the pelvic floor muscle of the patient.
2.5. Method 2.4, wherein the administering, applying or contacting comprises administering the calcium channel blocker, or L-arginine, or combination of a calcium channel blocker and L-arginine, or pharmaceutically acceptable salts thereof, to one or more specific trigger points in the pelvic floor muscle of the patient.

In further embodiments, the invention provides a method (Method 3) for treating sitting pain, post bowel movement pain, rectal pain, tailbone pain, urinary frequency, urinary urgency, urinary hesitancy, overactive bladder, perineal pain, penile pain, sexual dysfunction and reduced level of ejaculate or reduced penile erection in a patient comprising administering to the patient in need thereof a therapeutically effective amount of a calcium channel blocker, or L-arginine, or a combination of a calcium channel blocker and L-arginine, or pharmaceutically acceptable salts thereof, for example:
3.1. Method 3, wherein the calcium channel blocker is nifedipine or diltiazem;
3.2. Method 3 or 3.1, wherein the sitting pain, post bowel movement pain, rectal pain, tailbone pain, urinary frequency, urinary urgency, urinary hesitancy, overactive bladder, perineal pain, penile pain, sexual dysfunction and reduced level of ejaculate or reduced strength penile erection exists in the presence of pelvic floor muscle trigger points.
3.3. Any Method 3-3.2, wherein the administering, applying or contacting comprises administering the calcium channel blocker, or L-arginine, or combination of a calcium channel blocker and L-arginine, or pharmaceutically acceptable salts thereof, to the pelvic floor muscle of the patient.

3.4. Method 3.3, wherein the administering, applying or contacting comprises administering the calcium channel blocker, or L-arginine, or combination of a calcium channel blocker and L-arginine, or pharmaceutically acceptable salts thereof, to one or more specific trigger points in the pelvic floor muscle of the patient.

In further embodiments, the invention provides a method (Method 4) of treating myofascial pain in muscle tissue of a patient who has one or more trigger points in the muscle tissue comprising administering to the one or more trigger points of the patient in need thereof a therapeutically effective amount of a calcium channel blocker, or L-arginine, or a combination of a calcium channel blocker and L-arginine, or pharmaceutically acceptable salts thereof, for example:

4.1. Method 4, wherein the calcium channel blocker is nifedipine or diltiazem.

4.2. Method 4 or 4.1, wherein the administering, applying or contacting comprises administering the calcium channel blocker, or L-arginine, or combination of a calcium channel blocker and L-arginine, or pharmaceutically acceptable salts thereof, to the pelvic floor muscle of the patient.

4.3. Method 4.2, wherein the administering, applying or contacting comprises administering the calcium channel blocker, or L-arginine, or combination of a calcium channel blocker and L-arginine, or pharmaceutically acceptable salts thereof, to one or more specific trigger points in the pelvic floor muscle of the patient.

In further embodiments, the invention provides a method (Method 5) of reducing the pain/sensitivity of pelvic floor muscle trigger points detected upon palpation in a patient, comprising applying to the patient in need thereof a therapeutically effective amount of a calcium channel blocker, or L-arginine, or a combination of a calcium channel blocker and L-arginine, or pharmaceutically acceptable salts thereof, for example:

5.1. Method 5, wherein the calcium channel blocker is nifedipine or diltiazem.

5.2. Method 5 or 5.1, wherein the patient is a female.

5.3. Method 5.2, wherein the pelvic pain is not associated with hypertonus.

5.4. Any Method 5-5.3, wherein the administering, applying or contacting comprises administering the calcium channel blocker, or L-arginine, or combination of a calcium channel blocker and L-arginine, or pharmaceutically acceptable salts thereof, to the pelvic floor muscle of the patient.

5.5. Method 5.4, wherein the administering, applying or contacting comprises administering the calcium channel blocker, or L-arginine, or combination of a calcium channel blocker and L-arginine, or pharmaceutically acceptable salts thereof, to one or more specific trigger points in the pelvic floor muscle of the patient.

In further embodiments, the invention provides a method (Method 6) of treating pelvic pain in a female patient comprising administering to the patient in need thereof a therapeutically effective amount of a calcium channel blocker, or L-arginine, or a combination of a calcium channel blocker and L-arginine, or pharmaceutically acceptable salts thereof, for example:

6.1. Method 6, wherein the calcium channel blocker is nifedipine or diltiazem.

6.2. Method 6 or 6.1, wherein the pelvis of the female patient is not hypertonic.

6.3. Method 6 or 6.1, wherein the calcium channel blocker or l-arginine is not administered to the vagina of the patient.

6.4. Any Method 6-6.3, wherein the administering, applying or contacting comprises administering the calcium channel blocker, or L-arginine, or combination of a calcium channel blocker and L-arginine, or pharmaceutically acceptable salts thereof, to the pelvic floor muscle of the patient.

6.5. Method 6.4, wherein the administering, applying or contacting comprises administering the calcium channel blocker, or L-arginine, or combination of a calcium channel blocker and L-arginine, or pharmaceutically acceptable salts thereof, to one or more specific trigger points in the pelvic floor muscle of the patient.

In further embodiments, the invention provides a method (Method 7) of reducing or resolving trigger point pain, sensitivity or activity in muscle of a patient in need thereof comprising contacting the muscle with a therapeutically effective amount of a calcium channel blocker, or L-arginine, or a combination of a calcium channel blocker and L-arginine, or pharmaceutically acceptable salts thereof, for example:

7.1. Method 7, wherein the calcium channel blocker is nifedipine or diltiazem.

7.2. Method 7 or 7.1, wherein the therapeutically effective amount of a calcium channel blocker, or L-arginine, or a combination of a calcium channel blocker and L-arginine, or pharmaceutically acceptable salts thereof is administered on or near one or more external or internal trigger points of the muscle.

7.3. Method 7, 7.1 or 7.2, wherein the muscle is located in the anal sphincter, beyond the internal anal sphincter in the pelvic floor, in the superior portions of the levator ani muscles, in the coccygeus muscles, in the obturator internus muscles, in the internal portions of the piriformis; in an external muscle; in the rectus abdominus, in a gluteal muscle, in an adductor muscle, or the quadratus lumborum.

7.4. Any Method 7-7.3, wherein the contacting comprises injecting said calcium channel blocker, or L-arginine, or combination of a calcium channel blocker and L-arginine, or pharmaceutically acceptable salts thereof, into said muscle.

7.5. Method 7.4, wherein the contacting comprises injecting said calcium channel blocker, or L-arginine, or combination of a calcium channel blocker and L-arginine, or pharmaceutically acceptable salts thereof, directly into, near or adjacent to one or more trigger points of the muscle.

In further embodiments, the invention provides any of the foregoing Methods 1-6.5, wherein the contacting or administering comprises injecting the calcium channel blocker, or L-arginine, or combination of a calcium channel blocker and L-arginine, or pharmaceutically acceptable salts thereof, into a muscle; for example directly into, near or adjacent to one or more trigger points of the muscle. In some such embodiments, the calcium channel blocker, or L-arginine, or combination of a calcium channel blocker and L-arginine, or pharmaceutically acceptable salts thereof, is present in a pharmaceutical composition that further comprises one or more pharmaceutically acceptable carriers, and optionally an anesthetic.

In further embodiments, the invention provides any of the foregoing Methods 1-7.3, wherein the administering, applying or contacting of the calcium channel blocker is performed by ingestion of an oral dosage form comprising the calcium channel blocker, or pharmaceutically acceptable salt thereof; for example wherein the oral dosage form is a pill, a tablet, or a capsule.

In further embodiments, the invention provides any of the foregoing Methods 1-7.3, wherein the administering, applying or contacting of the calcium channel blocker is performed by application of a topical composition comprising the calcium channel blocker or L-arginine, or pharmaceutically acceptable salt thereof. In some embodiments, the administration or application of the topical pharmaceutical composition is intrarectal or perianal. In some embodiments, the topical composition comprising the calcium channel blocker, or L-arginine, or pharmaceutically acceptable salt thereof, contains a polyethylene glycol/polypropylene glycol block copolymer; for example a Poloxamer; for example Poloxamer 407P and/or Poloxamer 188P.

In further embodiments, the invention provides any of the foregoing Methods 1-7.5, wherein the calcium channel blocker is a dihyropyridine, a phenylalkylamine, a benzothiapene, zicotonide or a nonselective calcium channel blocker. In some embodiments, the dihydropyridine channel blocker is amlopidine, aranidipine, azelnidipine, barnidipine, benidipine, cilnidipine, clevidipine, isradipine, efonidipine, felodipine, lacidipone, lercanidipine, manidipine, nicardipine, nifedipine, nilvadipine, nimodipine, nisoldipine, nitrendipine, or pranidipine. In some embodiments, the phenylalkylamine calcium channel blocker is varapamil, gallopamil or fendiline. In some embodiments, the benzothiazepine calcium channel blocker is diltiazem. In some embodiments, the non-selective calcium channel blocker is mibefradil, bepridil, flunarizine, fluspirilene or fendiline. In some preferred embodiments, the calcium channel blocker is diltiazem or nifedipine, preferably nifedipine.

In further embodiments, the invention provides any of the foregoing Methods 1-7.5, wherein the method (Method 8) comprises administering to the patient in need thereof a pharmaceutical composition comprising the therapeutically effective amount of the calcium channel blocker, or L-arginine, or combination of a calcium channel blocker and L-arginine, or pharmaceutically acceptable salts thereof, for example:

8.1. Method 8, wherein the pharmaceutical composition further comprises a therapeutically effective amount of a local anesthetic.
8.2. Method 8 or 8.1, wherein the pharmaceutical composition further comprises a controlled release agent.
8.3. Any Method 8-8.2, wherein the pharmaceutical composition comprises a poloxamer.
8.4. Any Method 8-8.3, wherein the poloxamer is poloxamer 407®.
8.5. Any Method 8-8.4, wherein the pharmaceutical composition comprises diltiazem or nifedipine.
8.6. Any Method 8-8.5, wherein the pharmaceutical composition comprises nifedipine and a controlled release agent.
8.7. Any Method 8-8.6, wherein the pharmaceutical composition comprises diltiazem and a controlled release agent.
8.8. Any Method 8-8.7, wherein the pharmaceutical composition is topical.
8.9. Any Method 8-8.8, wherein the topical pharmaceutical composition is applied to a treatment site.
8.10. Method 8.9, wherein the treatment site is the inside of an anal opening or the pelvic floor muscles of the patient.
8.11. Method 8.9, wherein the treatment site is the vaginal opening of a female patient.
8.12. Any Method 8-8.11, wherein the topical pharmaceutical composition is applied manually, as a suppository, or using an applicator.
8.13. Method 8.12, wherein the topical pharmaceutical composition is applied using a disposable rectal syringe.
8.14. Method 8.12, wherein the topical pharmaceutical composition is applied using a reusable rectal syringe.
8.15. Any Method 8.8-8.14, further comprising administering an oral dose of a calcium channel blocker, for example nifedipine or diltiazem.
8.16. Method 8.15, wherein the oral dose of the calcium channel blocker is an oral dose of nifedipine.
8.17. Method 8.15, wherein the oral dose of nifedipine is an extended release dose.
8.18. Method 8.15, wherein the oral dose of nifedipine is an immediate release dose.
8.19. Method 8.8, wherein the topical pharmaceutical composition is applied to the anal sphincter or vaginal opening or cavity of the patient by inserting a pressure applicator device into a rectal cavity or a vaginal cavity of the human patient through the anal sphincter or vaginal opening; and applying pressure at an internal trigger point or area of myofascial restriction within the rectal cavity or the vaginal cavity with the pressure applicator device to apply the topical pharmaceutical composition while simultaneously doing trigger point release.
8.20. Any Method 8.8-8.15, wherein the pharmaceutical composition comprises the calcium channel blocker in an amount of from 0.5% to 5% by weight.
8.21. Any Method 8.8-8.15, wherein the pharmaceutical composition comprises the calcium channel blocker in an amount of from 0.5% to 4% by weight.
8.22. Any Method 8.8-8.15, wherein the pharmaceutical composition comprises the calcium channel blocker in an amount of about 1%; or about 2%, or about 3%, or about 4%, or about 5% by weight.
8.23. Any Method 8.16-8.18, wherein the calcium channel blocker is diltiazem or nifedipine.
8.24. Any Method 8.16-8.19, wherein the pharmaceutical composition comprises L-arginine in an amount of from 0.5% to 5% by weight; 0.5% to 4% by weight; 0.5% to 3% by weight; 0.5% to 2% by weight; or from 0.5% to 1.5% by weight; or about 0.5%, 1%, 1.5%, 2%, 2.5%, 3%, 4% or 5% by weight.

In further embodiments, the invention provides a Method (Method 9) for treating chronic pelvic pain, pelvic floor myalgia, pelvic floor dysfunction, interstitial cystitis, levator ani syndrome, coccygodynia, prostatodynia, piriformis syndrome, anal sphincter pain, bowel movement pain, post bowel movement pain, ejaculatory pain, post ejaculatory pain, sitting pain, post bowel movement pain, rectal pain, tailbone pain, urinary frequency, urinary urgency, urinary hesitancy, overactive bladder, perineal pain, penile pain, vaginismus, anismus, sexual dysfunction, reduced level of ejaculate or reduced penile erection, myofascial pain in muscle tissue of a patient who has one or more trigger points in the muscle tissue, or the pain/sensitivity of pelvic floor muscle trigger points and specific areas of myofascial restriction detected upon palpation in a patient; the method comprising:

a) palpating a patient to detect said trigger points: and
b) administering to the identified trigger points of the patient by the patient or therapist or another, a therapeutically effective amount of a calcium channel blocker, or L-arginine, or a combination of a calcium channel blocker and L-arginine, or pharmaceutically acceptable salts thereof, as described in any foregoing Method described herein.

In further embodiments, the invention provides a Method (Method 10) of treatment or self-treatment for the reduction and/or resolution of trigger point pain, sensitivity or activity in a muscle of a patient in need thereof, comprising administering a therapeutically effective amount of a calcium channel blocker, or L-arginine, or a combination of a calcium channel blocker and L-arginine, or pharmaceutically acceptable salts thereof to the muscle of the patient, for example:

10.1. Method 10, wherein the one or more trigger points are external trigger points.
10.2. Method 10 or 10.1, wherein the active agent is administered by injection.
0.3. Method 10-10.1, wherein the active agent is administered manually by the patient as part of a self-treatment program.
10.4. Any Method 10-10.2 wherein the active agent is administered directly to, near to, or adjacent to one or more trigger points of the muscle by the patient, doctor or physical therapist.

In further embodiments, the invention provides a Method (Method 11) for relieving external muscle soreness or pain comprising applying to the muscle a topical composition comprising a calcium channel blocker, or a pharmaceutically acceptable salt thereof, for example:

11.1. Method 11, wherein the topical pharmaceutical composition comprises diltiazem or nifedipine in an amount of from 0.5% to 5% by weight.
11.2. Method 11 or 11.1, wherein the topical pharmaceutical composition comprises diltiazem or nifedipine in an amount of about 1%; or about 2%, or about 3%; or about 4%, or about 5% by weight.
11.3. Any Method 11-11.2 wherein the topical pharmaceutical composition comprises diltiazem or nifedipine in an amount of about 1% by weight.
11.4. Any Method 11-11.3 wherein the topical pharmaceutical composition further comprises one or more of menthol, menthone, camphor, pulegol, isopulegol, cineole, mint oil, peppermint oil, spearmint oil, eucalyptus oil, 3-(1-menthoxy)propane-1,2-diol, N-alkyl-p-menthane-3-carboxamide, 2-methyl-3-(1-menthoxy)propane-1,2-diol, p-menthane-3,8-diol, 2-(1-menthoxy)ethan-1-ol, 3-(1-menthoxy)propan-1-ol, 4-(1-menthoxy)butan-1-ol, menthyl 3-hydroxybutanoate, menthyl lactate, menthone glycerin ketal, N-methyl-2,2-isopropylmethyl-3-methylbutane amide, menthyl glyoxylate cajuput oil, clove oil, dementholized mint oil and paraffin petrolatum.

In further embodiments, the invention provides a Method (Method 12) for relieving one or more symptoms of carpal tunnel syndrome, comprising administering to a patient in need thereof a pharmaceutical composition comprising a calcium channel blocker, or a pharmaceutically acceptable salt thereof, for example:

12.1. Method 12, wherein the patient is administered a topical pharmaceutical composition in accordance with any of Compositions 1-1.7 as described herein.
12.2. Method 12, wherein the patient is administered an oral pharmaceutical composition in accordance with any of Compositions 2-4 as described herein.
12.3. Method 12.1, further comprising administering a corticosteroid with the calcium channel blocker or pharmaceutically acceptable salts thereof.
12.4. Method 12.3, wherein the corticosteroid is cortisone or hydrocortisone, in an amount of from 0.01% to 5% by weight; 0.05% to 4% by weight; 0.1% to 4% by weight; 0.1% to 3% by weight; from 0.1% to 2% by weight; or from 0.5% to 1.5% by weight, or about 0.1%, 0.5%, 1%, 1.5%, 2%, 2.5%, 3%, 4% or 5% by weight.
12.5. Method 12, 1.1 or 12.3, wherein the topical composition is a balm, which is massaged into the muscle.

In further embodiments, the invention provides a Method (Method 13) for treatment of anal fissures, comprising perianal or intrarectal administration of a topical composition comprising a calcium channel blocker, or a pharmaceutically acceptable salt thereof, for example:

13.1. Method 13, wherein the calcium channel blocker is nifedipine or diltiazem.
13.2. Method 13, wherein the calcium channel blocker is nifedipine, and the method comprises administering a topical pharmaceutical composition comprising nifedipine in an amount of from 0.3-2%; wherein the topical composition comprises an excipient, which is optionally poloxamer 407.
13.3. Method 13, wherein the calcium channel blocker is diltiazem, and the method comprises administering a topical pharmaceutical composition comprising diltiazem in an amount of from 1% to 3%; wherein the topical composition comprises an excipient, which is optionally poloxamer 407.

In further embodiments, the invention provides a Method (Method 14) for treatment of anal fissures, comprising oral administration of a composition comprising a calcium channel blocker, or a pharmaceutically acceptable salt thereof, for example:

14.1. Method 14, wherein the calcium channel blocker is nifedipine or diltiazem.
14.2. Method 14 or 14.1, wherein the calcium channel blocker is nifedipine, in a dose of from 1-9 mg, or from 11-19 mg, or from 21-29 mg., or from 31-89 mg.
14.3. Method 14 or 14.1, wherein the calcium channel blocker is diltiazem, in a dose of from 2-4 mg.

In further embodiments, the invention provides a Method (Method 15) for treating a condition characterized by muscle spasm or soreness comprising administering to a patient in need thereof a therapeutically effective amount of a calcium channel blocker, or L-arginine, or a combination of a calcium channel blocker and L-arginine, or pharmaceutically acceptable salts thereof, for example:

15.1. Method 15, wherein the condition is selected from urinary sphincter spasms, urethral sphincter spasms, post urinary pain, rectal sphincter spasms and proctalgia fugax.
15.2. Method 15 or 15.1, comprising oral administration of the calcium channel blocker, or pharmaceutically acceptable salt thereof.
15.3. Any Method 15-15.2, comprising administration of an extended composition comprising the calcium channel blocker, or pharmaceutically acceptable salt thereof.
15.4. Any Method 15-15.3, wherein the calcium channel blocker is selected from nifedipine and diltiazem.

In further embodiments, the invention provides a Method (Method 16) for treating a condition selected from chronic pelvic pain, chronic pelvic pain without fissures or fistulas, chronically trigger pointed muscles, chronically trigger pointed pelvic floor muscles, chronic pelvic pain syndrome, pelvic floor myalgia, pelvic floor dysfunction, interstitial cystitis, levator ani syndrome, coccygodynia, prostatodynia, piriformis syndrome, vaginismus, anismus, anal sphincter pain, bowel movement pain, post bowel movement pain, ejaculatory pain or post ejaculatory pain; chronic pelvic pain without evidence of other pathology in external or internal anal sphincters; pelvic pain with pain referring trigger points; pelvic pain with associated with pelvic floor muscle trigger points and/or areas of myofascial restriction; sitting pain, post bowel movement pain, rectal pain, tailbone pain, urinary frequency, urinary urgency, urinary hesitancy, perineal pain, penile pain, vaginismus, anismus, sexual dysfunction and reduced level of ejaculate or reduced penile erection, urinary sphincter spasms, urethral sphincter spasms, post urinary pain, rectal sphincter spasms, proctalgia fugax and myofascial pain in muscle tissue of a patient who has one or more trigger points in the muscle tissue; the method comprising treating a patient in need thereof with a dilator, such as an anal, vaginal or urethral dilator (including pediatric dilators thereof), for example:

16.1. Method 16, wherein the dilator is an anal, vaginal, urethral or pediatric dilator.
16.2. Method 16, wherein the dilator has a diameter of from about ¼ inch to about 1½ inch, for example from about ¼ inch to about ¾ inch.
16.3. Method 16, wherein more then one dilator is used.
16.4. Method 16, wherein the method comprises progressive transitioning from smaller sized dilators to larger sized dilators.
16.5. Any Method 16-16.4, wherein the dilator or dilators are used daily, twice daily or three times daily, for a period of from about 10 minutes to about 40 minutes, or about 20 minutes to about 30 minutes.
16.6. Any Method 16-16.4, wherein the dilators are used on a single day, or for several days, or for a week, or for one month, or for several months.
16.7. Any Method 16-16.4, wherein the dilators are used until symptoms are resolved.
16.8. Any Method 16-16.4, further comprising the administration of a calcium channel blocker, or a pharmaceutically acceptable salt thereof, or a pharmaceutical composition thereof, prior to use of the dilator or dilators.
16.9. Method 16.8, wherein the calcium channel blocker, pharmaceutically acceptable salt thereof, or pharmaceutical composition thereof is administered orally for example, in the form of a pill, tablet or capsule; or topically (e.g., as a topical composition), such as an ointment, gel or paste.
16.10. Method 16.9, wherein the wherein the calcium channel blocker, pharmaceutically acceptable salt thereof, or pharmaceutical composition thereof is administered from 5 minutes to 60 minutes prior to dilator use.
16.11. Any Method 16-16.10, further comprising administration of an anesthetic.
16.12. Method 16.11, wherein the anesthetic is a component of the pharmaceutical composition containing the calcium channel blocker.
16.13. Any Method 16.8-16.12, wherein the calcium channel blocker is nifedipine.
16.14. Any Method 16.8-16.12, wherein the calcium channel blocker is administered in an oral or topical composition according to any of Compositions 1-5 herein.

In further embodiments, the invention provides any of the foregoing Methods 1-16, wherein the method (Method 17) further comprises administering a steroid with the calcium channel blocker, or L-arginine, or combination of calcium channel blocker and L-arginine, or pharmaceutically acceptable salts thereof, for example wherein the corticosteroid is cortisone or hydrocortisone, in an amount of from 0.01% to 5% by weight; 0.05% to 4% by weight; 0.1% to 4% by weight; 0.1% to 3% by weight; from 0.1% to 2% by weight; or from 0.5% to 1.5% by weight, or about 0.1%, 0.5%, 1%, 1.5%, 2%, 2.5%, 3%, 4% or 5% by weight.

In some embodiments of each of the foregoing Methods 1-17, the Methods comprise oral administration of a Composition comprising nifedipine in a dose of 1, 2, 3, 4, 5, 6, 7, 8, 9, 11, 12, 13, 14, 15, 16, 17, 18, 19, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, or 89 mg nifedipine. In some embodiments, the Composition is an extended release composition. In some embodiments, the composition is an immediate release composition.

In further embodiments, the invention provides the use of diltiazem, nifedipine, L-arginine or pharmaceutically acceptable salts thereof, to treat prostatitis category IIIA and/or IIIB in a male patient. In further embodiments, the invention provides the use of diltiazem, nifedipine, L-arginine or pharmaceutically acceptable salts thereof to treat chronic pelvic pain, chronic pelvic pain syndrome, pelvic floor myalgia, pelvic floor dysfunction, interstitial cystitis, levator ani syndrome, coccygodynia, prostatodynia, piriformis syndrome, vaginismus, anismus, anal sphincter pain, bowel movement pain, post bowel movement pain, ejaculatory pain or post ejaculatory pain.

In further embodiments, the invention provides the use of diltiazem, nifedipine, L-arginine or pharmaceutically acceptable salts thereof to treat sitting pain, post bowel movement pain, rectal pain, tailbone pain, urinary frequency, urinary urgency, urinary hesitancy, perineal pain, penile pain, sexual dysfunction and reduced level of ejaculate or reduced penile erection. In further embodiments, the invention provides the use of diltiazem, nifedipine L-arginine or pharmaceutically acceptable salts thereof to treat myofascial pain in muscle tissue of a patient who has one or more trigger points in the muscle tissue.

In further embodiments, the invention provides the use of diltiazem, nifedipine, L-arginine pharmaceutically acceptable salts thereof to reduce the pain/sensitivity of pelvic floor muscle trigger points detected upon palpation in a patient used topically and applied with a gloved finger of the patient manually. In further embodiments, the invention provides the use of diltiazem, nifedipine L-arginine or pharmaceutically acceptable salts thereof to treat pelvic pain in a female patient.

In further embodiments, the invention provides a topical pharmaceutical composition (Composition 1) comprising a calcium channel blocker, or L-arginine, or a combination of a calcium channel blocker and L-arginine, or pharmaceutically acceptable salts thereof, in a therapeutically effective amount, for example:

1.1. Composition 1, wherein the calcium channel blocker is nifedipine or diltiazem.
1.2. Composition 1 or 1.1, further comprising a poloxamer; for example poloxamer 407.
1.3. Any Composition 1-1.2, further comprising a local anesthetic, for example lidocaine.

1.4. Any Composition 1-1.3, comprising diltiazem or nifedipine in an amount of from 0.5% to 5% by weight.

1.5. Any Composition 1-1.4, comprising diltiazem or nifedipine in an amount of about 1%; or about 2%, or about 3%; or about 4%, or about 5% by weight.

1.6. Any Composition 1-1.5, comprising diltiazem or nifedipine in an amount of about 1% by weight.

1.7. Any Composition 1-1.6, comprising L-arginine in an amount of from 0.4% to 4% by weight.

1.8. Any Composition 1-1.3, comprising nifedipine or diltiazem in an amount therapeutically effective to treat one or more of chronic pelvic pain, chronic pelvic pain syndrome, pelvic floor myalgia, pelvic floor dysfunction, interstitial cystitis, levator ani syndrome, coccygodynia, prostatodynia, piriformis syndrome, anal sphincter pain, bowel movement pain, post bowel movement pain, vaginismus, anismus, ejaculatory pain, post ejaculatory pain, sitting pain, post bowel movement pain, rectal pain, tailbone pain, urinary frequency, urinary urgency, urinary hesitancy, perineal pain, penile pain, sexual dysfunction, reduced level of ejaculate or reduced penile erection, myofascial pain in muscle tissue of a patient who has one or more trigger points in the muscle tissue, conditions characterized by muscle spasm or soreness, urinary sphincter spasms, urethral sphincter spasms, post urinary pain, rectal sphincter spasms and proctalgia fugax, or the pain/sensitivity of pelvic floor muscle trigger points and specific areas of myofascial restriction detected upon palpation in a patient.

In further embodiments, the invention provides a pharmaceutical composition (Composition 2) for oral administration comprising nifedipine in an amount of from 1 to 89 mg nifedipine, for example 1, 2, 3, 4, 5, 6, 7, 8, 9, 11, 12, 13, 14, 15, 16, 17, 18, 19, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, or 89 mg nifedipine, for example:

2.1. Composition 2, comprising nifedipine in an amount of 1, 2, 3, 4, 5, 6, 7, 8 or 9 mg.

2.2. Composition 2, comprising nifedipine in an amount of 11, 12, 13, 14, 15, 16, 17, 18, 19, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, or 89 mg.

2.3. Composition 2, comprising nifedipine in an amount of 11, 12, 13, 14, 15, 16, 17, 18, or 19 mg.

2.4. Composition 2, comprising nifedipine in an amount of 21, 22, 23, 24, 25, 26, 27, 28, or 29 mg.

2.5. Composition 2, comprising nifedipine in an amount of 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88 or 89 mg.

2.6. Composition 2, comprising nifedipine in an amount of 3 mg, 5 mg, 6 mg, 9 mg, 12 mg, 15 mg, 18 mg, 21 mg, 24 mg, 25 mg, 27 mg or 29 mg of nifedipine.

2.7. Composition 2, comprising nifedipine in an amount of 32 mg, 35 mg, 38 mg, 40 mg, 41 mg, 45 mg, 48 mg, 50 mg, 55 mg, 58 mg, 62 mg, 65 mg, 70 mg, 75 mg, 80 mg, 85 mg or 89 mg of nifedipine.

2.8. Any Composition 2-2.7, wherein the composition is an immediate release composition.

2.9. Any Composition 2-2.7, wherein the composition is an extended release composition.

In further embodiments, the invention provides a pharmaceutical composition (Composition 3) for oral administration comprising diltiazem in an amount of 1, 2, 3, 6, 12, 15, 18, 21, 24 or 27 mg diltiazem. In some embodiments, the composition is extended release, and in other embodiments, the composition is immediate release. In further embodiments, the invention provides an extended release pharmaceutical composition (Composition 4) for oral administration comprising diltiazem in an amount of 1 mg to 170 mg; or 10 mg, 20 mg, 30 mg, 40 mg, 50 mg, 60 mg, 70 mg, 80 mg, 90 mg, 100 mg or 110 mg of diltiazem. In some embodiments, the composition is extended release, and in other embodiments, the composition is immediate release.

In further embodiments, the invention provides a composition (Composition 5) that is an extended release, enterically coated dosage form comprising an active ingredient that is a calcium channel blocker, wherein the dosage form additionally comprises one or more mucoadhesive polymers, and, optionally, one or more delayed release polymers, for example:

5.1. Composition 5, comprising a poloxamer.

In some embodiments, the invention provides a method for simultaneously delivering a systemic-acting and locally-acting dose of a calcium channel blocker, comprising administering to a patient in need there the dosage form of Composition 5 or 5.1.

In further embodiments, the invention provides Compositions 1-5 for use in treating pelvic pain disorders, such as prostatitis category IIIA and/or IIIB in a male patient, chronic pelvic pain, pelvic floor muscles with trigger points or areas of myofascial restriction, chronic pelvic pain syndrome, pelvic floor myalgia, pelvic floor dysfunction, interstitial cystitis, levator ani syndrome, coccygodynia, prostatodynia, prostadynia, piriformis syndrome, anal sphincter pain, bowel movement pain, post bowel movement pain, ejaculatory pain, ejaculatory discomfort, post ejaculatory pain, sitting pain, rectal pain, tailbone pain, urinary frequency, urinary urgency, urinary hesitancy, perineal pain, penile pain, vaginismus, anismus, sexual dysfunction, reduced level of ejaculate or reduced penile erection, non-bacterial prostatitis, slow urinary flow, reduced urinary flow, post ejaculatory discomfort, urinary or urethral sphincter spasms, post urinary pain, rectal sphincter spasms, proctalgia fugax, myofascial pain in muscle tissue of a patient who has one or more trigger points in the muscle tissue, and the pain/sensitivity of pelvic floor muscle trigger points and specific areas of myofascial restriction detected upon palpation in a patient.

The invention further provides each of the foregoing Methods 1-17, comprising administration of any foregoing Composition as described herein, e.g., Composition 1-5.1.

In some embodiments of each of the Methods 1-17 described herein, the methods further comprise the step of identifying a patient in need of said treatment.

In some embodiments of each of the Methods 1-17 described herein, the methods further comprise administration of an anesthetic, an anesthetic, for example a local anesthetic, for example lidocaine.

In some embodiments of each of the topical Compositions 1-1.8 and 5-5.1 described herein, the compositions can further comprise an anesthetic, for example a local anesthetic, for example lidocaine.

The present invention also provides an apparatus (Apparatus 1) for applying a topical pharmaceutical composition to a treatment site that is located within a rectal cavity or a vaginal cavity of a human patient, the apparatus comprising: a tubular member, wherein the topical pharmaceutical composition is located inside the tubular member prior to application of the topical preparation to the treatment site; and an applicator member that is receivable in the sleeve wherein, the applicator member is movable within the tubular member from a first position to a second position to cause at least a portion of the topical preparation to be moved out of the sleeve and thereby applied to the treatment site, for example:

1.1. Apparatus 1, wherein the tubular member is adapted to extend into an opening of the rectal cavity or the vaginal cavity of the human patient.

1.2. Apparatus 1, wherein the tubular member extends from a first end to a second end, wherein the first end is disposed within the rectal cavity or the vaginal cavity of the human patient during application of the topical pharmaceutical composition to the treatment site and the second end is disposed outside of the rectal cavity or the vaginal cavity of the human patient during application of the topical pharmaceutical composition to the treatment site.

1.3. Apparatus 1, wherein the tubular member extends from a first end to a second end, wherein the first end is disposed within the rectal cavity or the vaginal cavity of the human patient during application of the topical pharmaceutical composition to the treatment site and the second end is disposed outside of the rectal cavity or the vaginal cavity of the human patient during application of the topical pharmaceutical composition to the treatment site.

1.4. Apparatus 1.3, wherein the first end has a semi-spherical configuration defined by a plurality of segments that are movable in response to movement of the applicator member from the first position to the second position.

1.5. Apparatus 1, further comprising a stop surface that extends outward from the tubular member for restraining further insertion of the tubular member with respect to the rectal cavity or the vaginal cavity of the human patient.

The present invention also provides an apparatus (Apparatus 2) which is a drug applicator sleeve, the sleeve comprising:
a tubular member having an open end and a closed end; and
an integral conduit disposed thereon or therein;
wherein:
the tubular member has a length of from 2 to 10 inches, and a diameter of from ⅛ to 2 inches;
the integral conduit has a diameter of from ⅙ inch to 1 inch, and also optionally comprises a receiver for interfacing with a syringe, bulb or other reservoir, for example:

Further examples of Apparatus 2 according to the present invention include:

2.1. Apparatus 2, wherein the drug delivery sleeve is a smooth tube.

2.2. Apparatus 2 or 2.1, wherein the drug delivery sleeve is adapted to conform to the surfaces of a probe or trigger point wand.

2.3. Any apparatus 2-2.2, wherein the integral conduit comprises a receiver for interfacing with a syringe, bulb or other reservoir.

2.4. Any apparatus 2-2.3, wherein the integral conduit is prefilled with a pharmaceutical composition.

2.5. Apparatus 2.4, wherein the pharmaceutical composition is a Composition according to any of Compositions 1-5 described herein.

2.6. Any apparatus 2-2.5, wherein the integral conduit is disposed substantially along the length of the sleeve.

In further embodiments, the invention provides an assembly comprising a medical probe or trigger point wand and a drug applicator sleeve according to any of Apparatus 2-2.6.

In further embodiments, the invention provides kits comprising a disposable rectal syringe and a pharmaceutical composition according to any of Compositions 1-1.7. In further embodiments, the invention provides kits comprising a re-useable rectal syringe and a pharmaceutical composition according to any of Compositions 1-1.7. In further embodiments, the invention provides kits comprising an applicator as described herein, and a pharmaceutical composition according to any of Compositions 1-1.7. In some embodiments, the syringe or applicator of the kit is pre-filled with the pharmaceutical composition.

In some further embodiments, the invention provides kits comprising a plurality of dilators having sizes from about ¼ inch in diameter to about 1½ inch in diameter, or about ¼ inch in diameter to about ¾ inch in diameter, in size increments of 1/16 inch or ⅛ of an inch. In some embodiments, the kits further comprising an application guide, which provides instructions regarding the use of the dilators.

The following examples are further illustrative of the nature of the present invention, but it is understood that the invention is not limited thereto. All amounts and proportions referred to herein and in the appended claims are by weight, unless otherwise indicated.

Example 1—Preparation of Topical Formulation

Three ointment formulations are prepared that contain 1% diltiazem, 0.2-2% nifedipine and 1% L-arginine respectively as the active ingredient, each in an ointment containing poloxamer 407, and paraffin, or a transdermal vehicle or cream as known in the art for use as a carrier for active substances administered to the inside the anus or rectum.

Example 2—Preparation of Suppository Formulation

A base is prepared containing hydrogenated vegetable oil and PEG-8 Distearate. An appropriate amount of the base is weighed out and melted over low heat. Active (1% diltiazem or 0.2-2% nifedipine and/or 1% L-arginine) is weighed out. Silica gel is added and the combination is sifted into the melted base. The composition is then poured into suppository molds and cooled.

Example 2—Determination of Pelvic Floor Muscle Trigger Points and Specific Areas of Myofascial Restriction A patient's history is taken and the patient's pelvic pain related complaints are noted. A physical examination by a professional experienced in identifying and treating trigger points is done with knowledge of which trigger points are generally related to particular complaints. The professional then puts on an examining glove and examines tissue inside the anal sphincter and rectum of both men and women and inside the vagina in women, pressing on areas known to be related to particular symptoms. When a trigger point is felt (a tender band), a twitch is felt, the patient exhibits a 'jump response' and the symptom that the patient complains about is recreated, the trigger point is noted. The patient is later directed to apply nifedipine ointment, or diltiazem ointment, or L-arginine ointment for example in the area where trigger points were found.

Example 3—Administration of Topical Formulation

The topical formulation is administered to the patient's trigger points determined in example 2 above either manually, using a rectal syringe, or using the internal trigger point wand as described in, e.g. U.S. Pat. Nos. 8,337,435 and 8,224,464.

Example 4—Use of Dilators

Not wishing to be bound by any particular theory, pelvic pain, manifesting symptoms described in this application, is believed to be intimately related to the myofascial irritability, trigger points and areas of spasm in the pelvic floor. This can come from an injury or chronic tightening of the pelvic floor, not unlike an animal pulling its tail between its legs and tightening the pelvic floor in doing so, that with our without hypertonus, creates a constricted pelvic environment in which the shortened tissue in the pelvic floor and the resultant trigger points and areas of myofascial restriction refer pain to a variety of sites remote from the area of myofascial restriction. This can result in a ischemia in which blood flow is reduced in the sphincter, vaginal opening and pelvic floor. Nifedipine reduces calcium in the calcium channels and thereby relaxes the tissue, increases blood flow and reduces trigger point activity in the tissue.

What can augment the lengthening and rehabilitation of pelvic floor, the reduction of trigger points and the reduction of symptoms is the gradual microscopic lengthening of the contracted pelvic tissue with the use of a myofascial release aid called an anal and vaginal dilator. The dilator introduces in very small increments, a device that slowly stretches the sphincter and vagina from its hyperirritable and guarded state in a way that the sphincter and vagina can tolerate. Dilators of ¼" diameter are easily tolerated by the most hyperirritable orifices of a guarded anal sphincter or vaginal opening, and leaving the dilator in the orifice for 5-30 minutes while the patient practices relaxation of the area, in our clinical experience with certain patients, can give the patient a very clear sense of their own guarding and makes it easier for the patient to relax the guarded pelvic floor. The relaxation of this guarding typically leads to the release of the pelvic muscle spasm, the release of pelvic floor trigger points and the reduction of pain and symptoms. Once the sphincter is able to tolerate a very small diameter dilator, the next very small increment of size dilator is used. In a very painful and highly guarded anal sphincter or vagina, the progression of dilators changes every 3-4 weeks from ½" to ⅜" to ½", to ⅝" to ¾" to ⅞" to 1 inch to 1⅛ inch to 1¼ inch to 1⅜ in to 1½ inch. This slow increase in the stretch of the pelvic opening is under the patients control and is generally well tolerated and give the patient a sense of control over rehabilitation of their pelvic muscles. In combination with hot baths, the use of nifedipine, very gradual, non traumatic dilation and relaxation to lower autonomic arousal, progressive dilation is a powerful adjunct to the rehabilitation of a sore and painful pelvic floor.

While the invention has been described in connection with what is presently considered to be the most practical and preferred embodiment, it is to be understood that the invention is not to be limited to the disclosed embodiments, but to the contrary, it is intended to cover various modifications or equivalent arrangements included within the spirit and scope of the appended claims. The scope is to be accorded the broadest interpretation so as to encompass all such modifications and equivalent structures as is permitted under the law.

Each of the patents, books, articles and other printed publications referenced herein are incorporated by reference in their entireties for all purposes.

What is claimed is:

1. A method for reducing or resolving myofascial trigger point pain, sensitivity or activity in muscle of a patient in need thereof comprising contacting the muscle with a topical composition comprising a therapeutically effective amount of nifedipine, or a pharmaceutically acceptable salt thereof;
wherein the muscle is located in the pelvic floor, the anal sphincter, in the superior portions of the levator ani muscles, in the coccygeus muscles, in the obturator internus muscles, in the internal portions of the piriformis; in the rectus abdominus, in a gluteal muscle, in an adductor muscle, or the quadratus lumborum.

2. The method of claim 1, wherein the therapeutically effective amount of nifedipine or pharmaceutically acceptable salt thereof is administered on or near one or more internal trigger points of the muscle.

3. The method of 2, wherein said nifedipine or pharmaceutically acceptable salt thereof, is administered to the pelvic floor muscle of the patient, or to one or more specific trigger points in the pelvic floor muscle of the patient.

4. The method of claim 1, wherein the contacting of the nifedipine or pharmaceutically acceptable salt thereof with the muscle of the patient is performed by application of a topical composition comprising the nifedipine or pharmaceutically acceptable salt thereof either manually, or using a pressure applicator device.

5. The method of claim 4, wherein the topical composition comprises the nifedipine in an amount of from 0.5% to 5% by weight.

6. The method of claim 4, wherein the administration or application of the topical pharmaceutical composition is intrarectal or perianal.

7. The method of claim 4, wherein the topical composition comprising nifedipine or pharmaceutically acceptable salt thereof further comprises a polyethylene glycol/polypropylene glycol block copolymer.

8. The method of claim 7, wherein the polyethylene glycol/polypropylene glycol block copolymer comprises a Poloxamer.

9. The method of claim 7, wherein the polyethylene glycol/polypropylene glycol block copolymer comprises Poloxamer 407, Poloxamer 188, or both.

10. The method of claim 4, wherein the topical composition further comprises a controlled release agent.

11. The method of claim 4, wherein the topical composition is applied to a treatment site selected from the inside of an anal opening of a patient; the pelvic floor muscles of a patient; or the vaginal opening of a female patient.

12. The method of claim 4, wherein the topical composition further comprises a local anesthetic.

13. The method of claim 4, wherein the myofacial trigger point pain, sensitivity or activity is a symptom of a condition or disorder selected from prostatitis category IIIA and/or IIIB in a male patient, chronic pelvic pain, chronic pelvic pain without fissures or fistulas, pelvic floor muscles with trigger points or areas of myofascial restriction, chronic pelvic pain syndrome, pelvic floor myalgia, pelvic floor dysfunction, interstitial cystitis, levator ani syndrome, coccygodynia, prostatodynia, prostadynia, piriformis syndrome, anal sphincter pain, bowel movement pain, post bowel movement pain, ejaculatory pain, ejaculatory discomfort, post ejaculatory pain, sitting pain, rectal pain, tailbone pain, urinary frequency, urinary urgency, urinary hesitancy, perineal pain, penile pain, vaginismus, anismus, sexual dysfunction, reduced level of ejaculate or reduced penile erection, nonbacterial prostatitis, slow urinary flow, reduced urinary flow, post ejaculatory discomfort, urinary or urethral sphincter spasms, post urinary pain, rectal sphincter spasms, proctalgia fugax, myofascial pain in muscle tissue of a patient who has one or more trigger points in the muscle tissue, pain/sensitivity of pelvic floor muscle trigger points and specific areas of myofascial restriction detected upon palpation in a patient, chronically trigger pointed pelvic floor muscles, or overactive bladder.

14. The method of claim 4, wherein the myofacial trigger point pain, sensitivity or activity is a symptom of a condition or disorder selected from chronic pelvic pain, chronic pelvic pain without fissures or fistulas, chronically trigger pointed pelvic floor muscles, chronic pelvic pain syndrome, pelvic floor myalgia, pelvic floor dysfunction, interstitial cystitis, overactive bladder, levator ani syndrome, coccygodynia, prostatodynia, piriformis syndrome, anal sphincter pain, bowel movement pain, post bowel movement pain, vaginismus, anismus, ejaculatory pain or post ejaculatory pain in a patient; wherein the chronic pelvic pain exists with or without fissures or fistulas or evidence of hypertonus or other pathology in external or internal anal sphincters; and the chronic pelvic pain syndrome exists with pain containing or referring trigger points.

15. The method of claim 4, wherein the trigger point pain, sensitivity or activity is a symptom of a condition or disorder selected from sitting pain, post bowel movement pain, rectal pain, tailbone pain, urinary frequency, urinary urgency, urinary hesitancy, overactive bladder, perineal pain, penile pain, sexual dysfunction and reduced level of ejaculate or reduced penile erection.

16. The method of claim 4, wherein the topical pharmaceutical composition is applied to an internal trigger point in the body of the human patient by inserting a pressure applicator device into a rectal cavity or a vaginal cavity of the human patient through the anal sphincter or vaginal opening; applying the pharmaceutical composition to the trigger point using the pressure applicator device; and then performing trigger point release.

17. The method of claim 2, wherein the muscle is located beyond the internal anal sphincter in the pelvic floor.

\* \* \* \* \*